US009925043B2

(12) United States Patent
Vaturi

(10) Patent No.: US 9,925,043 B2
(45) Date of Patent: *Mar. 27, 2018

(54) DEVICE FOR PLACEMENT IN THE TRICUSPID ANNULUS

(71) Applicant: Trisol Medical Ltd., Yokneam (IL)

(72) Inventor: Mordehay Vaturi, Ganei-Tikva (IL)

(73) Assignee: Trisol Medical Ltd., Yokneam (JP)

( * ) Notice: Subject to any disclaimer, the term of this patent is extended or adjusted under 35 U.S.C. 154(b) by 48 days.

This patent is subject to a terminal disclaimer.

(21) Appl. No.: 15/066,051

(22) Filed: Mar. 10, 2016

(65) Prior Publication Data

US 2016/0184098 A1 Jun. 30, 2016

Related U.S. Application Data

(63) Continuation of application No. 14/359,646, filed as application No. PCT/IL2012/050469 on Nov. 21, 2012, now Pat. No. 9,445,893.

(60) Provisional application No. 61/561,986, filed on Nov. 21, 2011.

(51) Int. Cl.
*A61F 2/24* (2006.01)

(52) U.S. Cl.
CPC ................ *A61F 2/24* (2013.01); *A61F 2/246* (2013.01); *A61F 2/2409* (2013.01); *A61F 2/2412* (2013.01); *A61F 2/2454* (2013.01); *A61F 2/2463* (2013.01)

(58) Field of Classification Search
CPC ......... A61F 2/24; A61F 2/2412; A61F 2/2418
USPC .................................................. 623/2.1–2.19
See application file for complete search history.

(56) References Cited

U.S. PATENT DOCUMENTS

| | | | |
|---|---|---|---|
| 3,671,979 | A | 6/1972 | Moulopoulos |
| 4,218,783 | A | 8/1980 | Reul et al. |
| 4,553,533 | A | 11/1985 | Leighton |
| 4,561,129 | A | 12/1985 | Arpesella |
| 4,851,000 | A | 7/1989 | Gupta |

(Continued)

FOREIGN PATENT DOCUMENTS

| | | |
|---|---|---|
| CN | 101172059 | 5/2008 |
| WO | WO 2004/030568 | 4/2004 |

(Continued)

OTHER PUBLICATIONS

Communication Relating to the Results of the Partial International Search dated Nov. 20, 2013 From the International Searching Authority Re. Application No. PCT/IL2012/050469.

(Continued)

*Primary Examiner* — Suzette J Gherbi

(57) ABSTRACT

A device (200) for implantation in or near an annulus of a tricuspid valve comprising at least one blood flow control element (202) adapted to capture a volume of blood therein. Optionally or alternatively, the blood flow control element is adapted to allow at least some volume of blood (406) to regurgitate through the annulus during at least some part of systole. Optionally or alternatively, the device comprises a relatively rigid annulus with an arc length of less than 300 degrees. Optionally or alternatively, the relatively rigid annulus comprises a plurality of tissue fixation elements positioned along no more than 300 degrees of a circumference of the annulus, for example to avoid damaging conduction pathways between an atria and a chamber.

22 Claims, 16 Drawing Sheets

(56) References Cited

U.S. PATENT DOCUMENTS

| | | | | |
|---|---|---|---|---|
| 5,411,552 | A | 5/1995 | Andersen et al. | |
| 5,489,297 | A | 2/1996 | Duran | |
| 6,200,336 | B1 * | 3/2001 | Pavcnik | A61F 2/07 623/1.13 |
| 6,540,782 | B1 | 4/2003 | Snyders | |
| 6,989,027 | B2 | 1/2006 | Allen et al. | |
| 7,452,371 | B2 * | 11/2008 | Pavcnik | A61F 2/01 623/1.24 |
| 7,704,277 | B2 * | 4/2010 | Zakay | A61B 17/00234 623/2.1 |
| 8,460,370 | B2 | 6/2013 | Zakay et al. | |
| 8,932,348 | B2 * | 1/2015 | Solem | A61B 17/0401 623/2.11 |
| 9,445,893 | B2 * | 9/2016 | Vaturi | A61F 2/2412 |
| 2003/0199975 | A1 | 10/2003 | Gabbay | |
| 2005/0228495 | A1 | 10/2005 | Macoviak | |
| 2006/0058871 | A1 * | 3/2006 | Zakay | A61B 17/00234 623/2.18 |
| 2006/0241745 | A1 * | 10/2006 | Solem | A61F 2/246 623/2.18 |
| 2007/0005134 | A1 | 1/2007 | McCarthy | |
| 2007/0185571 | A1 | 8/2007 | Kapadia et al. | |
| 2007/0270943 | A1 * | 11/2007 | Solem | A61B 17/0401 623/2.11 |
| 2009/0099653 | A1 | 4/2009 | Suri et al. | |
| 2010/0174359 | A1 | 7/2010 | Hefti et al. | |
| 2010/0280606 | A1 | 11/2010 | Naor | |
| 2011/0022157 | A1 | 1/2011 | Essinger et al. | |
| 2011/0040374 | A1 | 2/2011 | Goetz et al. | |
| 2011/0077733 | A1 * | 3/2011 | Solem | A61F 2/24 623/2.12 |
| 2011/0264206 | A1 | 10/2011 | Tabor | |
| 2012/0035719 | A1 | 2/2012 | Forster et al. | |
| 2012/0323313 | A1 | 12/2012 | Seguin | |
| 2013/0226291 | A1 * | 8/2013 | Pavcnik | A61F 2/01 623/2.13 |
| 2013/0310928 | A1 | 11/2013 | Morriss et al. | |
| 2014/0135908 | A1 | 5/2014 | Glozman et al. | |
| 2014/0172083 | A1 | 6/2014 | Bruchman et al. | |
| 2014/0179993 | A1 * | 6/2014 | Alexander | A61B 17/0057 600/37 |
| 2014/0214159 | A1 | 7/2014 | Vidlund et al. | |
| 2014/0350662 | A1 * | 11/2014 | Vaturi | A61F 2/2412 623/2.1 |

FOREIGN PATENT DOCUMENTS

| | | |
|---|---|---|
| WO | WO 2004/089250 | 10/2004 |
| WO | WO 2005/027797 | 3/2005 |
| WO | WO 2010/108079 | 9/2010 |
| WO | WO 2013/022798 | 2/2013 |
| WO | WO 2013/076724 | 5/2013 |
| WO | WO 2014/021905 | 2/2014 |
| WO | WO 2014/022124 | 2/2014 |
| WO | WO 2016/098104 | 6/2016 |

OTHER PUBLICATIONS

International Preliminary Report on Patentability dated Jun. 5, 2014 From the International Bureau of WIPO Re. Application No. PCT/IL2012/050469.

International Search Report and the Written Opinion dated Feb. 3, 2014 From the International Searching Authority Re. Application No. PCT/IL2012/050469.

Notice of Allowance dated Dec. 14, 2015 From the U.S. Patent and Trademark Office Re. U.S. Appl. No. 14/359,646.

Official Action dated Jun. 19, 2015 From the U.S. Patent and Trademark Office Re. U.S. Appl. No. 14/359,646.

Anwar et al. "Assessment of Tricuspid Valve Annulus Size, Shape and Function Using Real-Time Three-Dimensional Echocardiography", Interactive Cardio Vascular and Thoracic Surgery, 5: 683-687, 2006.

Colombo et al. "Tricuspid Regurgitation Secondary to Mitral Valve Disease: Tricuspid Annulus Function as Guide to Tricuspid Annulus Function as Guide to Tricuspid Valve Repair", Cardiovascular Surgery, 9(4): 369-377, 2001.

Dini et al. "Right Ventricular Dysfunction Is a Major Predictor of Outcome in Patients With Moderate to Severe Mitral Regurgitaiton and Left Ventricular Dysfunction", American Heart Journal, 154: 172-179, 2007.

Dreyfus et al. "Secondary Tricuspid Regurgitation or Dilatation: Which Should Be the Criteria for Surgical Repair?", The Annals of Thoracic Surgery, 79(1): 127-132, Jan. 2005.

Dreyfus et al. "Tricuspid Leaflet Augmentation to Address Severe Tethering in Functional Tricuspid Regurgitation", European Journal of Cardio-Thoracic Surgery, 34(4): 908-910, Oct. 2008.

Engstroem et al. "Right Ventricular Dysfunction Is an Independent Predictor for Mortality in ST-Elevation Myocardial Infarction Patients Presenting With Cardiogenic Shock on Admission", European Journal of Heart Failure, 12: 276-282, 2010.

Fukuda et al. "Tricuspid Valve Tethering Predicts Residual Tricuspid Regurgitation After Tricuspid Annuloplasty", Circulation, 111: 975-979, Mar. 1, 2005.

Ghanta et al. "Suture Bicuspidization of the TTricuspid Valve Versus Ring Annuloplasty for Repair of Functional Tricuspid Regurgitation: Midterm Results of 237 Consecutive Patients", The Journal of Thoracic and Cardiovascular Surgery, 133(1): 117-126, Jan. 2007.

Guenther et al. "Tricuspid Valve Surgery: A Thirty-Year Assessment of Early and Late Outcome", European Journal of Cardio-Thoracic Surgery, 34: 402-409, 2008.

Gurvitch et al. "Transcatheter Valve-in-Valve Implantation for Failed Surgical Bioprosthetic Valves", Journal of the American College of Cardiology, 58(21): 2196-2209, 2011.

Kim et al. "Assessment of Haemodynamic Effects of Surgical Correction for Severe Functional Tricuspid Regurgitation: Cardiac Magnetic Resonance Imaging Study", European Heart Journal, 31: 1520-1528, 2010.

Lancellotti et al. "European Association of Echocardiolography Recommendations for the Assessment of Valvular Regurgitation. Part 2: Mitral and Tricuspid Regurgitaiton (Native Valve Disease)", European Journal of Echocardiography, 11: 307-332, 2010.

McCarthy et al. "Tricuspid Valve Repair: Durability and Risk Factors for Failure", The Journal of Thoracic and Cardiovascular Surgery, 127(3): 674-685, Mar. 2004.

Nath et al. "Impact of Tricuspid Regurgitation on Long-Term Survival", Journal of the American College of Cardiology, JACC, 43(3): 405-409, 2004.

Navia et al. "Surgical Management of Secondary Tricuspid Valve Regurgitation: Annulus, Commissure, or Leaflet Procedure?", The Journal of Thoracic and Cardiovascular Surgery, 139(6): 1473-1482e5, Jun. 2010.

Porter et al. "Tricuspid Regurgitation Late After Mitral Valve Replacement: Clinical and Echocardiographic Evaluation", The Journal of Heart Velve Disease, 8(1): 57-62, Jan. 1999. Abstract.

Roberts et al. "Percutaneous Tricuspid Valve Replacement in Congenital and Acquired Heart Disease", Journal of the American College of Cardiology, 58(2): 117-122, 2011.

Sengupta et al. "RV Form and Function. A Piston Pump, Vortex Impeller, or Hydraulic Ram?", Journal of the American College of Cardiology, JACC: Cardiovascular Imaging, 6(5): 636-639, May 2013.

Taramasso et al. "The Growing Clinical Importance of Secondary Tricuspid Regurgitation", Journal of the American College of Cardiology, JACC, 59(8): 703-710, 2012.

Tei et al. "The Tricuspid Valve Annulus: Study of Size and Motion in Normal Subjects and in Patients With Tricuspid Regurgitation", Circulation, 66(3): 665-671, Sep. 1982.

International Search Report and the Written Opinion dated Jul. 26, 2016 From the International Searching Authority Re. Application No. PCT/IL2015/051210.

Invitation to Pay Additional Fees dated May 5, 2016 From the International Searching Authority Re. Application No. PCT/IL2015/51210.

(56) References Cited

OTHER PUBLICATIONS

International Preliminary Report on Patentability dated Jun. 29, 2017 From the International Bureau of WIPO Re. Application No. PCT/IL2015/051210. (6 Pages).

* cited by examiner

Systole

Diastole

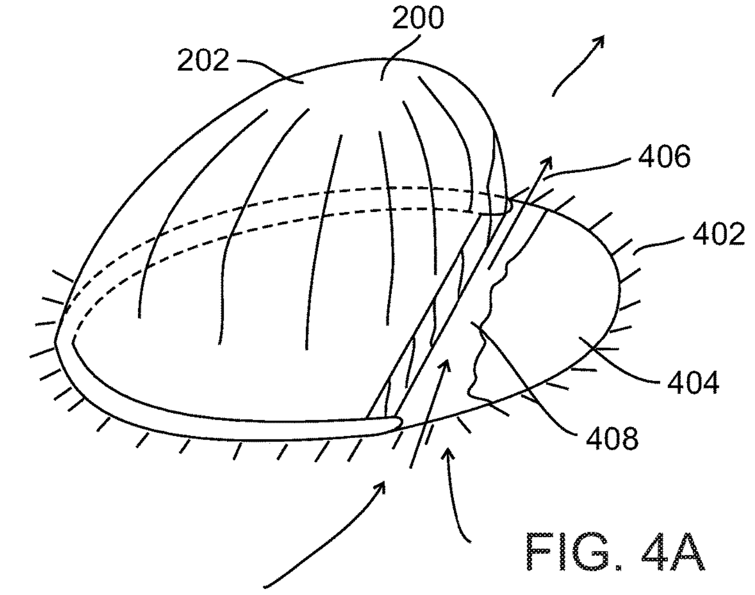
FIG. 4A
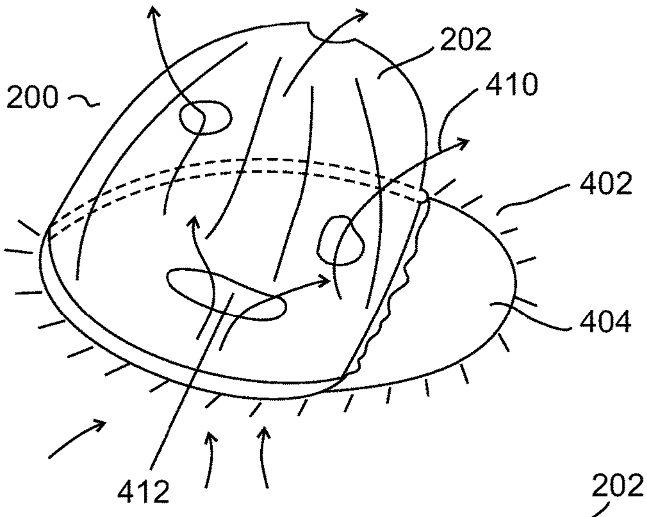
FIG. 4B
FIG. 4C
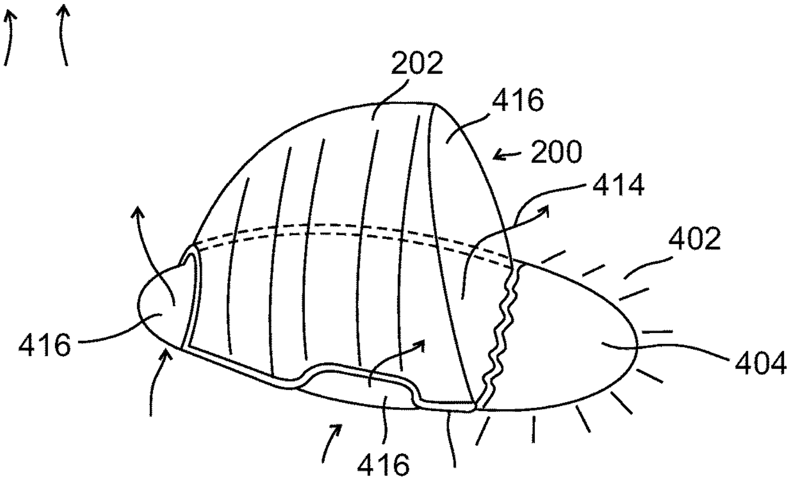

DEVICE FOR PLACEMENT IN THE TRICUSPID ANNULUS

RELATED APPLICATIONS

This application is a continuation of U.S. patent application Ser. No. 14/359,646 filed on May 21, 2014, which is a National Phase of PCT Patent Application No. PCT/IL2012/050469 filed on Nov. 21, 2012, which claims the benefit of U.S. Provisional Patent Application No. 61/561,986 filed on Nov. 21, 2011. The contents of the above applications are all incorporated by reference as if fully set forth herein in their entirety.

FIELD AND BACKGROUND OF THE INVENTION

The present invention, in some embodiments thereof, relates to an implantable medical device and, more particularly, but not exclusively, to a device for implantation in a tricuspid annulus of a patient.

In US Patent Application No. 2007/0005134, McCarthy discloses "An apparatus for implantation in the annulus of a tricuspid valve has an anterior annulus aspect, a posterior annulus aspect, and an atrioventricular (AV) node located adjacent the anterior annulus aspect."

Lancellotti P et al., "European Association of Echocardiography recommendations for the assessment of valvular regurgitation. Part 2: mitral and tricuspid regurgitation (native valve disease)" Eur J Echocardiogr. 2010 May; 11(4): 307-32. disclose "standards for the assessment of mitral and tricuspid regurgitation".

U.S. Pat. No. 7,291,168 described a device having a half sewing ring with a membrane which serves as a neo-annulus or a neo-leaflet.

Additional background art includes:

US Application No. 2006/0122686;

US Application No. 2006/0122693;

US Application No. 2012/0136436;

US Application No. 2008/0262609;

US Application No. 2010/0286767;

Nath J, Foster E, Heidenreich P A. Impact of tricuspid regurgitation on long-term impact. J Am Coll Cardiol 2004; 43:405-409;

Dreyfus G D, et al. Secondary tricuspid regurgitation or dilatation: which should be the criteria for surgical repair? Ann Thorac Surg 2005; 79:127-132;

Navia J L, et al. Surgical management of secondary tricuspid valve regurgitation: Annulus, commissure, or leaflet procedure? J Thorac Cardiovasc Surg 2010; 139:1473-1482;

McCarthy P M, Bhudia S K, Rajeswaran J, et al. Tricuspid valve repair: durability and risk factors for failure. J Thorac Cardiovasc Surg. 2004; 127:674-85;

Dreyfus G D, Raja S G, Chan K M. Tricuspid leaflet augmentation to address severe tethering in functional tricuspid regurgitation. Eur J Cardiothorac Surg 2008; 34:908-910; and Ghanta R K, et al. Suture bicuspidization of the tricuspid valve versus ring annuloplasty for repair of functional tricuspid regurgitation: midterm results of 237 consecutive patients. J Thorac Cardiovasc Surg. 2007; 133:117-26.

SUMMARY OF THE INVENTION

An aspect of some embodiments of the invention relates to an implantable device for reducing regurgitation from the right ventricle to the right atrium. Optionally, the device allows at least some volume of blood to regurgitate and/or collects some blood during systole, so as to increase the chamber volume. In an exemplary embodiment of the invention, the prosthesis does not touch and/or pierce through the atrioventricular node and/or bundle of His.

There is provided in accordance with an exemplary embodiment of the invention a device for implantation at or near an annulus of a tricuspid valve comprising at least one blood flow control element adapted to capture a volume of blood therein. Optionally, said capture comprises capture during at least a portion of systole.

In an exemplary embodiment of the invention, said device is configured to release said captured volume into a right ventricle during diastole.

In an exemplary embodiment of the invention, said blood flow control element is convex.

In an exemplary embodiment of the invention, said blood flow control element is a sail.

In an exemplary embodiment of the invention, said volume of blood is between 5 and 20 ml. Optionally, said volume of blood is held by said control element in an atria.

In an exemplary embodiment of the invention, said volume of blood is at least 8 mL.

In an exemplary embodiment of the invention, said device is adapted for allowing at least some blood to regurgitate through said annulus during systole. Optionally, said at least some blood is between 3 and 25 mL. Optionally or alternatively, a total area for said blood regurgitation is no more than 20 $mm^2$.

In an exemplary embodiment of the invention, said device is sized to allow blood regurgitation between said element and a native tricuspid leaflet. Optionally or alternatively, said element comprises one or more apertures for said regurgitation.

In an exemplary embodiment of the invention, said element changes configuration during systole and diastole so that said captured volume is at least twice as high during systole.

In an exemplary embodiment of the invention, said element is configured to resist flow into an atria during systole and substantially does not inhibit flow into a ventricle during diastole.

In an exemplary embodiment of the invention, said device comprises one or more members adapted to retain most of said blood flow control element in an atrial aspect of said device during diastole.

In an exemplary embodiment of the invention, said device has a size sufficient to replace one or two native tricuspid leaflets when implanted in said annulus.

In an exemplary embodiment of the invention, said device has a size sufficient to preserve function of one or two native tricuspid leaflets when said device is placed in said annulus. Optionally, said size of said device is sufficiently short to preserve function of a septal leaflet. Optionally or alternatively, said native tricuspid leaflets allow blood to flow through said annulus during diastole.

In an exemplary embodiment of the invention, said blood flow control element is adapted to allow at least some blood flow to flow from a right atrium to a right ventricle through said annulus during diastole.

In an exemplary embodiment of the invention, the device comprises a support element adapted to contact at least a portion of said annulus, said element coupled to said support element. Optionally, said support structure has an incomplete circumference. Optionally or alternatively, said incomplete circumference is between 180 and 300 degrees.

Optionally or alternatively, said blood flow control element spans at least 90% of said incomplete circumference.

In an exemplary embodiment of the invention, said support element is radially expandable.

In an exemplary embodiment of the invention, said device comprises a plurality of tissue fixation elements, said elements located along no more than 270 degrees along a circumference of said device, leaving a gap of at least 7 mm. Optionally, at least some of said elements are positioned to fixate to a ventricular aspect of said annulus. Optionally or alternatively, at least some of said elements are positioned to fixate to an atrial aspect of said annulus.

In an exemplary embodiment of the invention, said support element has a non-symmetrical shape and said support element is adapted to have an open contiguous area of at least 1 $cm^2$, said contiguous area is adapted to be placed towards a coronary sinus.

In an exemplary embodiment of the invention, said device is sized to maintain a gap of at least 3 mm between said element and at least one remaining functional tricuspid leaflet, said gap along at least 50% of a length of said leaflet.

There is provided in accordance with an exemplary embodiment of the invention a device for replacing at least one leaflet of a tricuspid valve, said device comprising:

- a relatively rigid annulus, said annulus having an arc length of between 180 degrees and 300 degrees; and
- a blood flow control element for controlling flow, said element coupled to said rigid annulus, wherein said element resists flow less for flow from the atria than for flow from the ventricle.

There is provided in accordance with an exemplary embodiment of the invention a device for replacing a tricuspid valve, said device comprising:

- a relatively rigid annulus, said annulus comprising a plurality of tissue fixation elements adapted to pierce tissue or otherwise interfere with conduction in-fixed to tissue, positioned along no more than 300 degrees of a circumference thereof; and
- a prosthetic valve or part thereof coupled to said annulus.

There is provided in accordance with an exemplary embodiment of the invention a method of percutaneously deploying a device in an annulus of a tricuspid valve comprising expanding said device without said device contacting a membranous septum when in an implanted state. Optionally, said device is deployed without contacting at least one of an atrioventricular node and a bundle of His. Optionally or alternatively, said deploying comprises unrolling said device along said annulus. Optionally or alternatively, said device comprises a blood flow control element in a pleated state prior to said expanding.

There is provided in accordance with an exemplary embodiment of the invention a method of treating tricuspid regurgitation comprising percutaneously deploying a device, said device comprises a blood flow control element adapted to temporarily store blood from the ventricle in an atria, in said element, and/or allow a reduced amount of regurgitation through or past the device, in a tricuspid annulus of a subject in need of treatment thereof. Optionally, the method comprises selecting said device to reduce an amount of regurgitated blood by 30%-80%, thereby treating said regurgitation.

Optionally or alternatively, the method comprises selecting said device to temporarily capture at least 50% of regurgitated blood, thereby treating said regurgitation.

Optionally or alternatively, the method comprises modifying a volume of captured blood by adjusting said device.

Optionally or alternatively, the method comprises modifying a volume of blood regurgitated into an atria by adjusting said device.

There is provided in accordance with an exemplary embodiment of the invention a device for implantation in the annulus of a tricuspid valve comprising at least one blood flow element adapted to allow at least 3 ml of blood to regurgitate through said annulus during at least some part of a systole.

There is provided in accordance with an exemplary embodiment of the invention a method of operation of a device for implantation in the annulus of a tricuspid valve comprising:

capturing at least some volume of regurgitated blood in a blood flow control element during at least some part of systole; and releasing at least some volume of said captured blood into a right ventricle during at least some part of diastole.

There is provided in accordance with an exemplary embodiment of the invention a method of percutaneously deploying a device in an annulus of a tricuspid valve comprising deploying the device without significantly altering the function of one or two native tricuspid leaflets such that the device controls blood flow through the annulus.

In an exemplary embodiment of the invention, the method further comprises expanding the device against at least one of an anterior and posterior native leaflets.

There is provided in accordance with an exemplary embodiment of the invention the one or two native tricuspid leaflets comprise a septal leaflet.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 4A-4C are illustrations of selective regurgitation by the tricuspid device, in accordance with an exemplary embodiment of the invention;

DESCRIPTION OF SPECIFIC EMBODIMENTS OF THE INVENTION

Figure 1A:
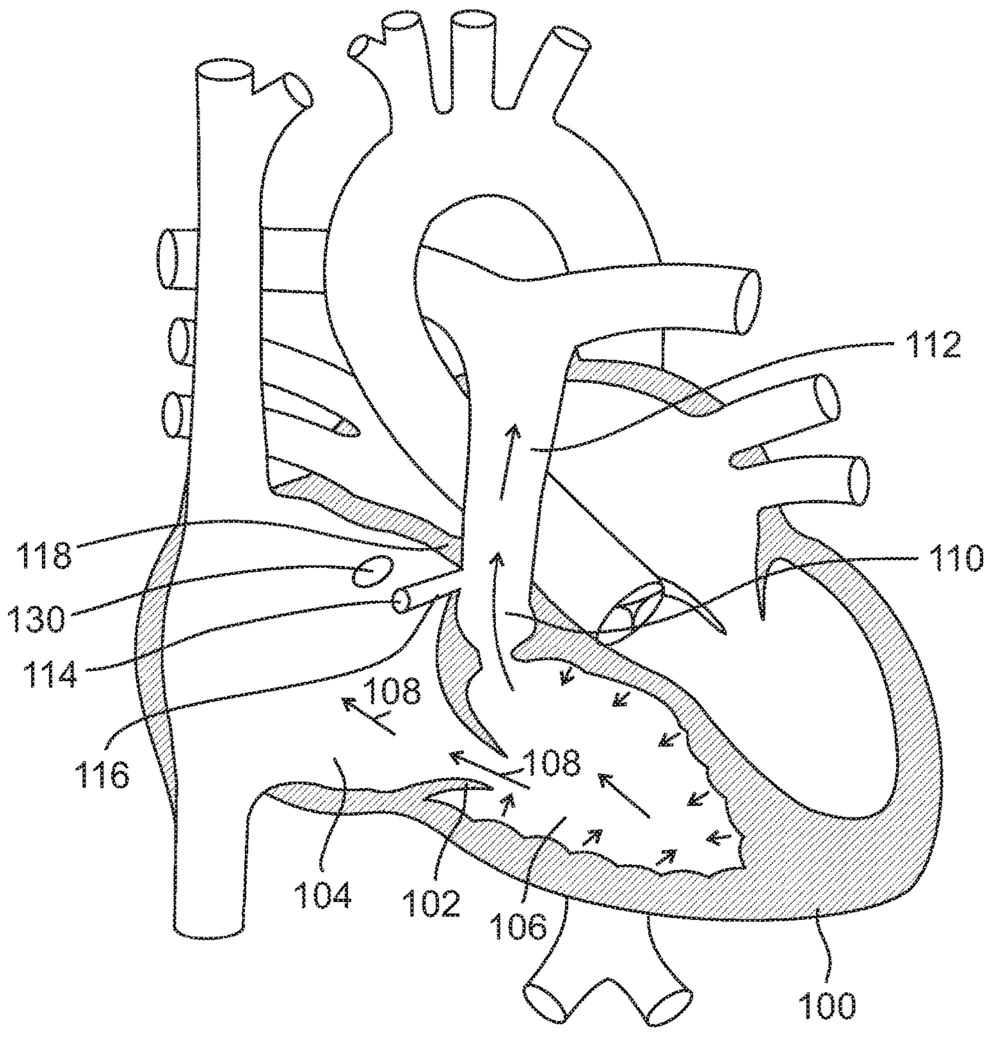
FIG. 1A is an illustration of a heart of a patient suffering from tricuspid regurgitation, useful in understanding some embodiments of the invention.

The present invention, in some embodiments thereof, relates to an implantable medical device and, more particularly, but not exclusively, to a device for implantation in a tricuspid annulus of a patient.

An aspect of some embodiments of the invention relates to an implantable blood flow altering device, such as a prosthetic tricuspid device, for reducing excessive blood flow (e.g., regurgitation) from the right ventricle to the right atrium. In an exemplary embodiment of the invention, at least some volume of blood is allowed to regurgitate or at least leave the right ventricle, such as during the systolic phase of the cardiac cycle, for example, to provide a tradeoff between damage to various body tissues, damage to the heart from over working and insufficient cardiac output. Optionally, at least some of the blood is not allowed to leave the heart, optionally preventing or reducing damage to veins and/or other tissue in the body. In some embodiments of the invention two types of regurgitation are supported: regurgitation back to the atria and regurgitation into a blood collecting element which inhibits blood flow into the atria itself, but which may store such inhibited blood, at least temporarily, in the atria.

In an exemplary embodiment of the invention, the amount of regurgitation or partial regurgitation (e.g., leaving the ventricle but not the heart) is selected to prevent over-taxing of the right ventricle. As such, it may depend on the health of the right ventricle. Optionally or alternatively, the amount of regurgitation is selected to not be sufficient to damage the veins or other tissues of the body. Optionally or alternatively, the amount of regurgitation or partial regurgitation is selected to be small enough so that a useful stroke volume is provided. Optionally, the temporal profile of regurgitation is modified by the device and the device is optionally selected for that. For example, the blood flow control element may expand and after expansion block or reduce further regurgitation. In another example, apertures are provided so that regurgitation can continue all through systole.

In an exemplary embodiment of the invention, the volume of blood that is regurgitated out of the right ventricle during systole is reduced by 50%-95% (e.g., relative to the regurgitated volume before implantation of the device), by 60%-80%, by 50%-70%, by 70%-90%, or other smaller, intermediate or larger ranges are used. Optionally, forward flow is not reduced. Alternatively, forward flow is reduced by 20-90%, by 30%-70%, by 40%-60%, or other smaller, intermediate or larger ranges are used. Optionally, forward flow is increased, for example, by 10%, 30%, 50%, 100% or intermediate or greater percentages. In an exemplary embodiment of the invention, such changes in flow volume are provided by selecting device characteristics according to patient condition. For example, for patients with overt RV failure a valve with a greater blood capture (hence smaller forward flow) is used and vice versa for patients with preserved RV contraction.

In an exemplary embodiment of the invention, a blood flow control element captures at least some of the regurgitated volume, blocks at least part of the regurgitated volume, and/or allows at least some blood to pass. Optionally, the blood flow control element is selected according to current regurgitation and/or health of the right ventricle and/or expected shock to the body if sudden changes in regurgitation occur. The blood flow control element captures at least 90% of the blood volume being regurgitated from the right ventricle to the right atrium during systole or at least 70%, at least 50%, at least 30% of the regurgitated volume or other smaller, intermediate or largest values are used. Alternatively or additionally, the blood flow control element captures at least 70 mL of the regurgitated volume, or at least 60 mL, at least 50 mL, at least 45 mL, at least 35 mL, at least 25 mL, at least 15 mL, or other smaller, intermediate or larger values are used. Optionally, in an exemplary embodiment of the invention, the captured volume is at least 1 ml, at least 3 ml, at least 5 ml or, for example, between 8 and 10 ml. In an exemplary embodiment of the invention, the volume is at least twice the volume (if any) captured outside the ventricle in a natural or artificial valve.

In some embodiments of the invention, the capture is absolute, in that no blood bypasses the device. In other embodiments, blood passes by the captured volume or the captured volume includes one or more apertures through which blood can escape into the atria.

In an exemplary embodiment of the invention, the blood flow control element is sack-like and is configured to extend into the atria when pressure increases in the ventricle. Optionally, flow from the atria into ventricle is substantially uninhibited by the device, for example, with the device collapsing from flow in that direction.

In an exemplary embodiment of the invention, there is one blood flow control element. Alternatively, there are a plurality of blood flow control elements, for example, 2, 3, 4, 5, or other larger numbers of elements are used. Optionally, one element defines one or more sub-elements adapted to control blood flow, for example, to capture at least some volume of blood. Each element comprises 1 sub-element, or 2, 3, 4, 5, or other larger number of sub-elements are used.

Optionally, the element is designed to prevent stagnation of blood, thereby possibly reducing the risk of blood coagulation, for example, by temporarily trapping the blood during the systolic phase. Optionally, the regurgitated volume is released back into the right ventricle, such as during the diastolic phase. Optionally, the element is designed to collapse from an atrial side towards a ventricular side, optionally with an opening remaining in the ventricular side, so that as it collapses, blood is pushed out of the element and into the ventricle and possibly prevents pooling. Optionally or alternatively, the element includes one or more apertures, which prevent blood pooling therein.

In an exemplary embodiment of the invention, at least some of the volume of blood which is trapped, is caught in the right atrium by the device, for example by the blood flow control element. Optionally, the rest of the volume remains in the ventricle. At least some of the trapped blood is prevented from flowing upstream out of the atrium (and/or ventricle), such as into the inferior and/or superior vena cava and/or upstream blood vessels (such as causing flow reversal in the hepatic vein). At least 50% of the total trapped volume is caught in the right atrium (optionally the rest of the blood remains in the ventricle and/or is allowed to regurgitate), or 60%, 70%, 80%, 90%, 100%, or other smaller, intermediate or larger values are used.

In an exemplary embodiment of the invention, the volume captured by the device is selected as a function of stroke volume, for example, between 15 and 50% of the stroke volume, for example, between 20 and 40% thereof. In an exemplary embodiment of the invention, a healthy heart, a smaller amount needs to be captured, while in a diseased right ventricle, more blood needs to be captured to avoid over stressing the right ventricle.

In an exemplary embodiment of the invention, it is noted that the capture device effectively increases the volume of the right ventricle, for example, by between 10% and 60%, for example between 20% and 40% (e.g., 25%: 10 ml for a stroke volume of 40%). Optionally, the % increase is selected so as to reduce the actual amount of blood that the right ventricle needs to expel in a given beat. In some embodiments, the increase in volume in the right ventricle is only during systole, in effect, capping the amount of contraction and ejection fraction achievable.

In an exemplary embodiment of the invention, two separate functions are provided by the device. First, capping the amount of blood moved by the ventricle and second, capping the maximal pressure achieved in the right ventricle. Optionally, the maximal pressure is capped, mainly, by allowing some regurgitation, while ejection fraction is capped, mainly, by the volume captured by the device. It is noted, that each of the two functions is provided, in part at least, by the regurgitation and/or by the capture volume. Provision of a controlled amount of regurgitation may also temporally spread and/or slow down the increase in venous pressure during systole.

In an exemplary embodiment of the invention, the tricuspid device does not reduce the diameter of the native annulus, for example, the device is designed to function within a dilated annulus. Optionally, the tricuspid device expands the diameter of the native annulus, for example, in a stenotic tricuspid valve. Optionally, the native valve is not repaired. Optionally, part of the native valve is replaced, such as one or two native leaflets.

In an exemplary embodiment of the invention, the volume that will be trapped by the blood flow control element depends on the direction of flow between the atria and the ventricle, for example, causing a variation in blood capture throughout the cardiac cycle. Optionally, the volume of the element is relatively smaller, possibly substantially zero in diastole than in systole, for example, the element is a sail that collapses during diastole, or the element is elastic. Optionally, the collapsed element stores no more than 20% of the blood relative to the expanded state, or no more than 10%, 30%, 50%, 70%, or other smaller, intermediate or larger percentages are used. Optionally, the element does not enter into the right ventricle, for example, prevented by biasing elements. Optionally, the volume of blood that can be captured by the element is relatively increased during systole, such as to capture the regurgitated volume, for example, by an element such as the expandable sail. Optionally, the element expands into the right atrium, for example, the sail expands into the right atrium.

In an exemplary embodiment of the invention, the blood flow control element is designed to substantially allow blood flow past it during diastole, optionally collapsing at the start of diastole and/or optionally expanding and capturing blood only after systole starts.

In an exemplary embodiment of the invention, the blood flow element is convex. Optionally, the blood flow element, when collapsed becomes flat, for example, due to having a substantial degree of flexibility. In an exemplary embodiment of the invention, the element flattens against a wall of the heart, for example, against the wall of the right ventricle.

In an exemplary embodiment of the invention, the tricuspid device allows for the regurgitation of at least some blood from the right ventricle to the right atrium during systole. In an exemplary embodiment of the invention, the volume of blood that is selectively allowed to regurgitate out of the right ventricle during systole is reduced to be below 45 mL, below 35 mL, below 25 mL, below 15 mL, below 5 mL, or other smaller, intermediate or larger values are used. In an exemplary embodiment of the invention, at least a certain average amount of regurgitation into the atria, per beat at rest is provided, for example, at least 1 ml, at least 3 ml, at least 5 ml. Optionally or alternatively, the desired amount of regurgitation is selected for a non-rest time, for example, during weak or during strenuous exercise. In an exemplary embodiment of the invention, the device is designed so regurgitation takes place along the entire systole. In some embodiments, the regurgitation will peak in early systole and will diminish or stop once the sail is filled with blood and expands, due to a reduction in effective regurgitation orifice becomes smaller. In other embodiments, for example, where the sail has apertures and/or where the sail is distorted and pulled away from the existing leaflets by filling, regurgitation may increase after filling.

In an exemplary embodiment of the invention, blood is regurgitated between the blood flow control element and one or more native leaflets. Alternatively or additionally, blood is regurgitated through the element, such as through one or more holes. Alternatively or additionally, blood is regurgitated between the element and the annulus or device support. Optionally, in some cases, as the heart heals, the leaflet is expected to close against the device.

In an exemplary embodiment of the invention, the effective size of the total area (e.g., during systole) that is provided for blood to regurgitate from the right ventricle to the right atrium is less than 40 $mm^2$, less than 30 $mm^2$, less than 20 $mm^2$, less than 10 $mm^2$, less than 5 $mm^2$, or other smaller, intermediate or larger values are used. Optionally, the effective size is at least 1 $mm^2$, 3 $mm^2$, 5 $mm^2$ or smaller or intermediate or greater sizes. An aspect of some embodiments of the invention relates to a prosthetic tricuspid device that allows a sufficient amount of blood flow to enter the right ventricle from the right atrium during diastole. Blood flows through the atrioventricular annulus under a low pressure gradient, such as about 1 mmHg, about 3 mmHg, about 5 mmHg, about 10 mmHg, about 15 mmHg, about 20 mmHg, or other smaller, intermediate or larger pressure gradients. The effective orifice area to allow the blood flow is at least 0.2 $cm^2$, at least 0.4 $cm^2$, at least 0.6 $cm^2$, at least 0.8 $cm^2$, at least 1.0 $cm^2$, at least 1.2 $cm^2$, at least 1.4 $cm^2$, at least 1.6 $cm^2$, at least 1.8 $cm^2$, at least 2.0 $cm^2$, or other smaller, intermediate or larger values are used.

In an exemplary embodiment of the invention, one or more native leaflets are preserved, for example, by not deploying the device on the leaflets. The remaining one or more leaflets or parts thereof are replaced, such as by the prosthetic device. Optionally, the native septal leaflet is preserved. Optionally, the anterior and/or posterior septal leaflets are rendered non-functional by the deployment of the device.

In an exemplary embodiment of the invention, the native leaflet and optional other remaining leaflet are urged by the blood flowing into the right ventricle during diastole to increase the effective orifice area during diastole. Optionally, the prosthetic device has an effect of reducing the natural effective orifice area, for example, if the leaflet of the blood flow control element is rigid enough so as not to be urged by the inflowing blood. Independently, implantation of the device may shrink or expand the valve annulus, for example, by selecting a device annulus diameter greater or smaller than natural.

In some embodiments, the leaflet of the blood flow control element is at least partially urged by the flowing blood to increase the effective orifice area during systole. In some embodiments, blood flows through the blood flow control element into the ventricle (e.g., through one or more holes in the blood flow control element).

In an exemplary embodiment of the invention, the native leaflet and the blood flow control element of the prosthetic device do not contact. A gap of at least 1 mm is maintained, or 3 mm, 5 mm, 7 mm, 10 mm, or other smaller, intermediate or larger values are used. Optionally, the gap is less than, for example, 7 mm, 5 mm or 3 mm. Alternatively, the native leaflet and the prosthetic device coapt at least at one region, for example along about 25% of the length of the blood flow control element, or along about 50%, 75%, 100%, or other smaller, intermediate or larger values are used.

An aspect of some embodiments of the invention relates to a prosthetic tricuspid device, that comprises an outer circumference of less than 360 degrees, for example, about 345 degrees, or 330 degrees, 315 degrees, 300 degrees, 270 degrees, 240 degrees, 180 degrees, or 120 degrees, or other, smaller, intermediate or larger values are used. In a non-circular annulus, the angular extent is defined by projecting the annulus onto a smallest enclosing circle.

Optionally or additionally, the length of the 'missing' outer circumference arc is about 3 mm, about 5 mm, about 7 mm, about 10 mm, about 15 mm, about 20 mm, about 25 mm, about 30 mm, or other smaller, intermediate or larger lengths are used. In an exemplary embodiment of the invention, the device has an annulus section extending at least 180, 200, 220, 250, 300 or smaller or intermediate or greater degrees. In an exemplary embodiment of the invention, the device includes a flap or blood blocking element attached to the annulus and which extends at least 180, 200, 220, 250, 300 or smaller or intermediate or greater degrees. In an exemplary embodiment of the invention, the flap is designed to coapt with an existing natural flap. Optionally, the flap includes a blood flow control element which extends after coapting (or possibly near coaptation, in case of designed regurgitation into the atria). Optionally, the flap is convex. Optionally or alternatively, the flap is large enough to act as a flap valve which covers most or all of the natural valve and/or leaflets thereof. In one example, the leaflet has a conical form. In another example, the leaflet is bag like with, for example, the shape of part of a sphere or ovoid.

In an exemplary embodiment of the invention, the flap attached to the device over more than 180 degrees does not act symmetrically with respect to flow. Specifically, in an exemplary embodiment of the invention, the flap provides more resistance and/or more blood capturing for retrograde flow than for flow from the atria into the ventricle.

In an exemplary embodiment of the invention, the diameter (e.g., major and/or minor) of the outer circumference of the prosthetic device is sufficiently large to fit a normal or dilated annulus diameter. The diameter is about 22 mm, about 24 mm, about 26 mm, about 28 mm, about 30 mm, about 32 mm, about 34 mm, about 36 mm, about 38 mm, about 40 mm, about 42 mm, about 44 mm, about 46 mm, about 48 mm, about 50 mm, or other smaller, intermediate or larger diameters are used. Optionally, the shape of the remaining outer circumference is substantially the shape of the native annulus, such as elliptical or ovoidal, optionally non-planar, such as saddle shaped (e.g., having two high points oriented superiorly towards the right atrium).

In an exemplary embodiment of the invention, the missing section is sufficiently large to prevent contact with at least part of the septal wall comprising the atrioventricular node and/or bundle of His.

In an exemplary embodiment of the invention, the missing section is sufficiently large to preserve one native tricuspid leaflets. Alternatively, the missing section is sufficiently large to preserve two native tricuspid leaflets. At least one of the preserved leaflets is the septal leaflet.

In an exemplary embodiment of the invention, the prosthetic device augments the function of one or more remaining leaflets of the native tricuspid valve. For example, the remaining leaflets continue to function, such as to move away from the device to let blood flow into the ventricle (e.g., diastole) and/or to coapt with the device to block blood out of the ventricle (e.g., systole).

An aspect of some embodiments of the invention relates to a prosthetic tricuspid device that comprises a contiguous portion along the outer circumference without anchoring elements that pierce and/or forcefully contact tissue in a manner which could interfere with the functionality of underlying conductive tissue. The arc length of the segment without elements is about 15 degrees, or 30 degrees, 45 degrees, 60 degrees, 90 degrees, 120 degrees, or other smaller, intermediate or larger values are used. Optionally or alternatively, the arc length is about 3 mm, about 5 mm, about 7 mm, about 10 mm, about 15 mm, about 20 mm, about 25 mm, about 30 mm, or other smaller, intermediate or larger values are used.

In an exemplary embodiment of the invention, contiguous means an attachment element every 20 degrees or less. In some embodiments, contiguous means an attachment element every 10 mm or less, such as every 8 mm or 7 mm or less.

In an exemplary embodiment of the invention, lack of suturing is less of a problem if the device includes a resilient element larger in diameter than the annulus and which resists passage of the device as a whole into the atria during systole.

In other embodiments, the flap is allowed to evert into the right ventricle. However, flow from the atria is not necessarily undesirably impeded as the other leaflets do not contact it.

In other embodiments, the device annulus lies on the atrial side of the valve. Optionally, the existing attachments (e.g., sutures, pins, clips), at least near the gap, are designed (e.g., size, strength) to compensate for lack of nearby attachment mechanism.

In an exemplary embodiment of the invention, the section without elements is the same length as the section missing from the outer circumference.

In an exemplary embodiment of the invention, anchoring elements fixate to tissue, such as the native leaflets, the commissural area and/or muscle tissue of the atrium and/or ventricle. Some non-limiting examples of fixation include; by friction, by an adhesive (e.g., glue), pinching the tissue. Optionally, elements pierce tissues. Optionally, elements do not perforate tissue. Non-limiting examples of piercing depth include; no more than 1 mm, 2 mm, 3 mm, 5 mm, 7 mm, 10 mm, or other smaller, intermediate or larger values are used.

In an exemplary embodiment of the invention, the anchoring elements are sized and/or shaped to prevent perforation of the myocardium and/or septum. Optionally or additionally, the anchoring elements are sized and/or shaped to prevent perforation of vascular structures, such as the right coronary artery.

In an exemplary embodiment of the invention, at least some of the anchoring elements are shaped to fixate to the atrial aspect of tissues of the atrioventricular annulus, for example, to pierce the atrial aspect. Alternatively or additionally, at least some of the anchoring elements are shaped to fixate to the ventricular aspect of the tissues of the atrioventricular annulus, for example, to fixate to the ventricular aspect.

An aspect of some embodiments of the invention relates to a method of treating a heart of a patient comprising implanting a prosthetic device in the atrioventricular annulus. Optionally, the method comprises replacing and/or overlying at least one or two leaflets or portions thereof with the prosthetic device and preserving the remaining one or two leaflets. Additionally or alternatively, the method comprises positioning the prosthetic device in the annulus without touching and/or perforating an area of a septum comprising the AV node and/or bundle of His.

An aspect of some embodiments of the invention relates to a method of treating a patient with tricuspid regurgitation, in which a device or valve is implanted (e.g., and accordingly sized and/or selected) in a tricuspid valve or the tricuspid valve is otherwise repaired, such that at least some regurgitation is intentionally maintained. Optionally, the amount of maintained regurgitation is selected to prevent a shock or overstrain to the right ventricle. Optionally, the amount of regurgitation is modified at a later time, for example, increased or reduced, according to the patient condition.

An aspect of some embodiments of the invention relates to a prosthetic device for transcatheter placement in the annulus of the native tricuspid valve. The device is percutaneously deployed at the junction of the right atrium and right ventricle.

In an exemplary embodiment of the invention, the device comprises a blood flow control element (e.g., sail, valve, pocket) attached to a support structure. The support element is expandable from a compressed state to an expanded state. Optionally, the support element expands to a non-continuous circumference. Alternatively or additionally, the device is expanded by rolling the device, for example along the annulus, such as from a rolled state to an unrolled state. Alternatively or additionally, the blood flow control element is expanded from being arranged in pleats to the expanded state.

An aspect of some embodiments of the invention relates to a method to anchor a tricuspid device (e.g., a blood capturing device as described herein or a valve or part of a valve) without contacting and/or piercing the AV node and/or bundle of His. In an exemplary embodiment of the invention, the tricuspid device is unrolled and/or expanded around the annulus, starting in a direction away from the septum.

In an exemplary embodiment of the invention, the support element does not block blood flow out of the coronary sinus into the right atrium, thereby possibly maintaining adequate blood flow through the coronary circulation. Optionally, the support element is sized so as not to block blood flow. Alternatively, a region of the support element is shaped so as not to block blood flow, such as by a section of support element having a large enough hole to allow blood flow from the coronary sinus through the support element. In an exemplary embodiment of the invention, the area of the hole is about 50% of the area of the coronary sinus, or about 75%, about 100%, about 125%, about 150%, about 200%, or other smaller, intermediate or larger areas are used. The element being short enough to allow blood flow or the support element having one or more holes sufficiently large to allow blood flow. In an exemplary embodiment of the invention, a variety of support structures are available for the different variations in anatomical locations of the coronary sinuses. Optionally, the support structure is based on the anatomy, for example, according to ultrasound imaging and/or fluoroscopic studies of the anatomy.

In an exemplary embodiment of the invention, the support element is expanded to anchor to the atrial aspect of the annulus. Optionally or additionally, the support element is expanded to anchor to the ventricular aspect of the annulus. Alternatively, the support is expanded to anchor against the annulus itself, for example, against the leaflets or against an existing prosthetic device. In some embodiments, anchoring is achieved using a wire shell. Optionally, the support element is compressed in an alternating biased pattern, so that when expanded, anchoring elements fixate to the atrial and/or ventricle aspects.

An aspect of some embodiments of the invention relates to a device adapted to support healing and/or remodeling of the right ventricle. In some cases, the sudden increase of volume in the right atrium can overwork the heart. For example, the right ventricle may be weak and unable to pump the additional volume to the lungs. In another example, the left ventricle may be weak, being unable to handle the additional volume coming from the right side of the heart. In still another example, there may be difficulty in filling the left side of the heart (e.g., mitral stenosis), and an increase in the blood from the right side may overload the lungs with fluid.

In an exemplary embodiment of the invention, the device does not stop regurgitation (e.g., from the right ventricle to the right atrium during at least some part of systole) all at once. Optionally, the regurgitation allows enough blood to escape the right ventricle so as not to overload the right ventricle. Alternatively or additionally, the regurgitation allows enough blood to escape the right ventricle so as not to overload the left ventricle. Alternatively or additionally, the regurgitation allows enough blood to escape the right ventricle so as not to overload the circulatory system of the lungs.

In an exemplary embodiment of the invention, the regurgitation and/or other device parameters, such as captured volume allowed by the device is adjusted after implantation, for example, according to the healing of the right and/or left ventricle. Optionally, the regurgitation allowed is increased. Alternatively, the regurgitation allowed is decreased.

A potential advantage of a device according to some embodiments of the invention, over a valve, is that a tradeoff between blood flow to lungs and flow back to vena cava can be provided.

A potential advantage of a device according to some embodiments of the invention, over a valve, is that traumatization (due to change in flow dynamics) to the circulatory system and especially the right ventricle can be reduced. In a typical case of changing of the tricuspid valve, the sudden increase in possible stroke volume and/or afterload and/or right ventricular pressure may overload the right ventricle. This can cause collapse of the right ventricular function.

A potential advantage of a device according to some embodiments of the invention is for sub-acute compromises in right ventricular (RV) function, the device may allow a favorable hemodynamics that may prevent or delay further deterioration in RV function.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Overview

Referring now to the drawings, FIG. 1A illustrates a heart 100 of a patient suffering from regurgitation of a tricuspid valve 102, useful in understanding some embodiments of the invention. Leaflets of valve 102 fail to sufficiently coapt during the systolic phase of the cardiac cycle, for example, due to a dilated annulus and/or due to tethering of the leaflets and/or due to remodeling of a right ventricle 106. Blood flow 108 during contraction of right ventricle 106 (shown as small arrows in ventricle) is at least partially directed to a right atrium 104. In patients that do not suffer from tricuspid regurgitation, a competent tricuspid valve prevents and/or limits blood flow from ventricle 106 to atrium 104 during ventricular contraction. Most or all of a normal blood flow 110 is directed from ventricle 106 to pulmonary arteries 112.

Signals to cause contraction of right ventricle 106 and a left ventricle are conducted through an atrioventricular node 114 (located in atrioventricular part of membranous septum 118) and through bundle of His 116. Signals are shown as small arrows around AV node 114. When surgically replacing tricuspid valve 102, there is a risk of disrupting right ventricle 106 and left ventricle contraction signals, such as due to needles and/or sutures piercing AV node 114 and/or bundle of His 116.

Exemplary Prosthesis

Figure 1B:
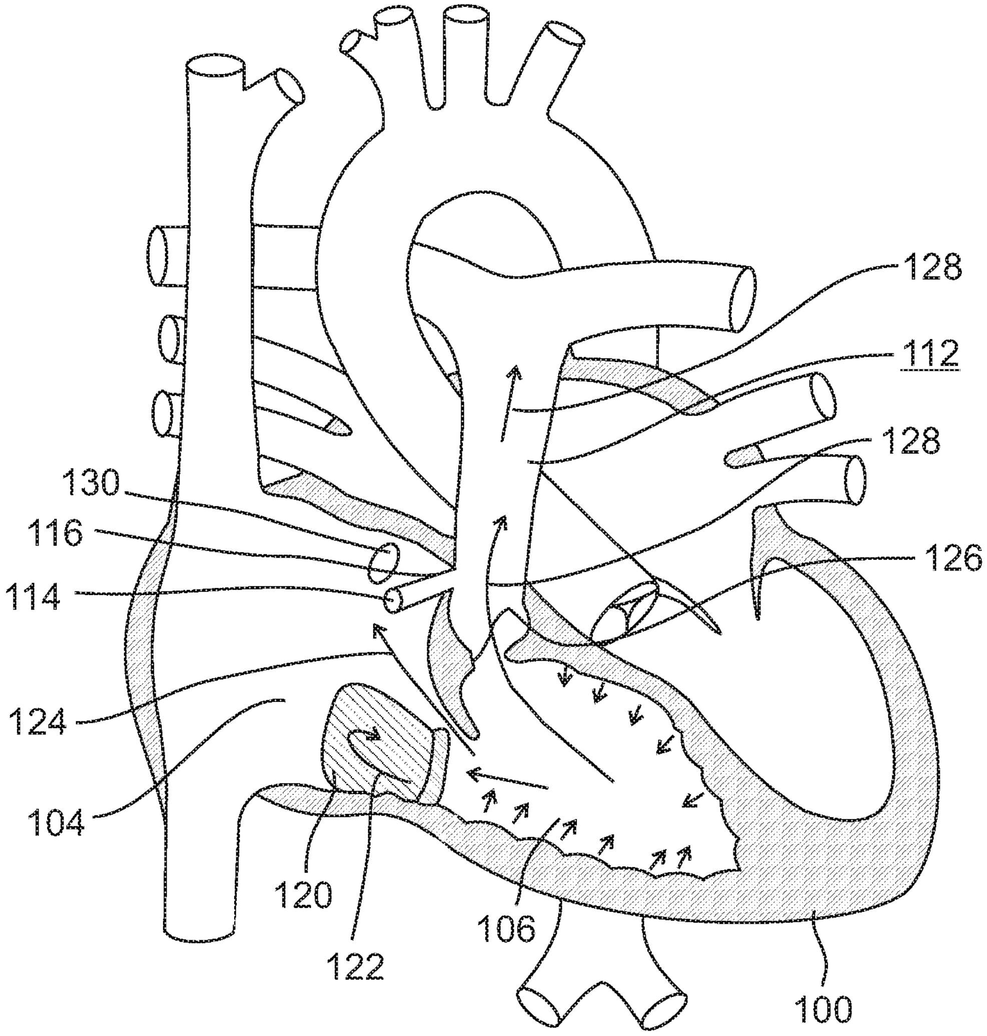
FIGS. 1B-1C are illustrations of a tricuspid device inside the heart during diastole and systole, in accordance with an exemplary embodiment of the invention.
Figure 1C:
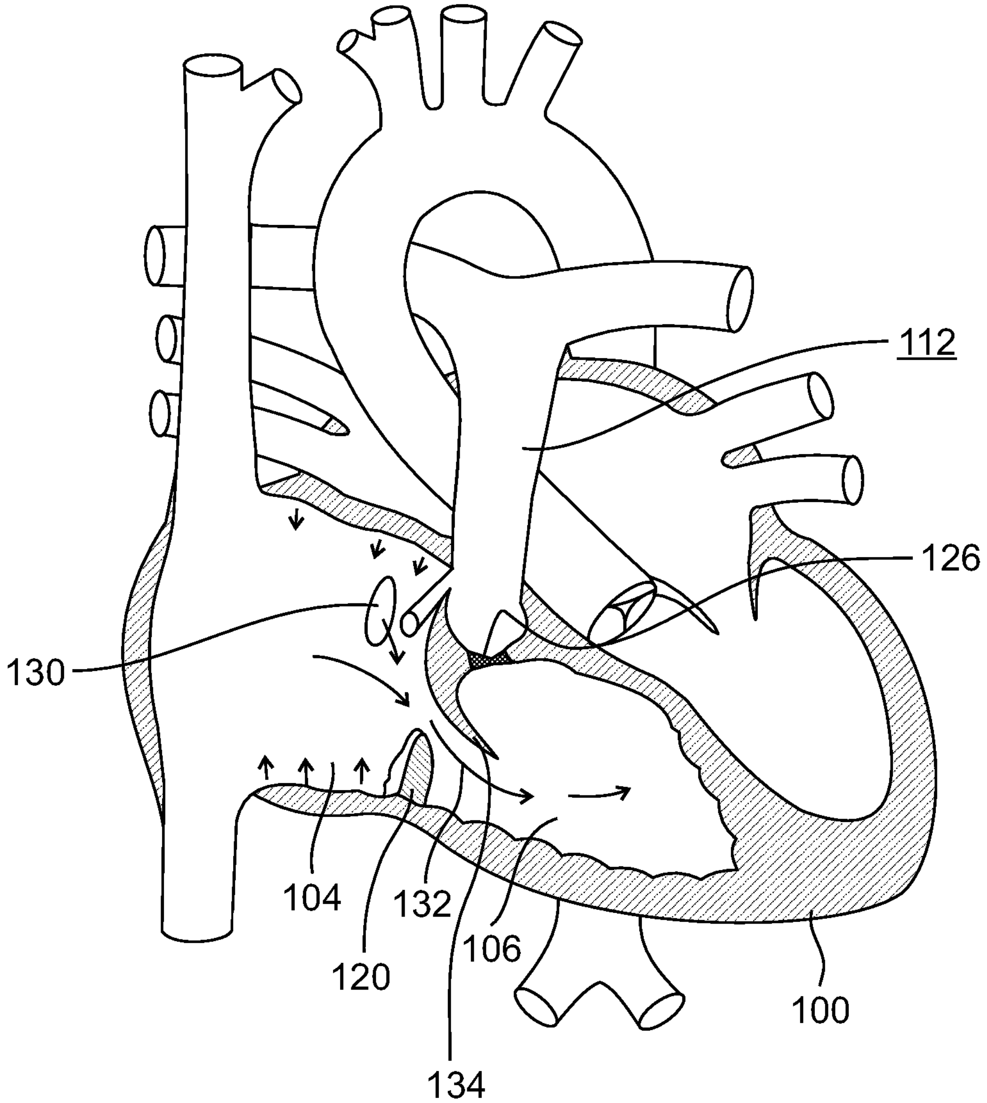
Figure 2A:
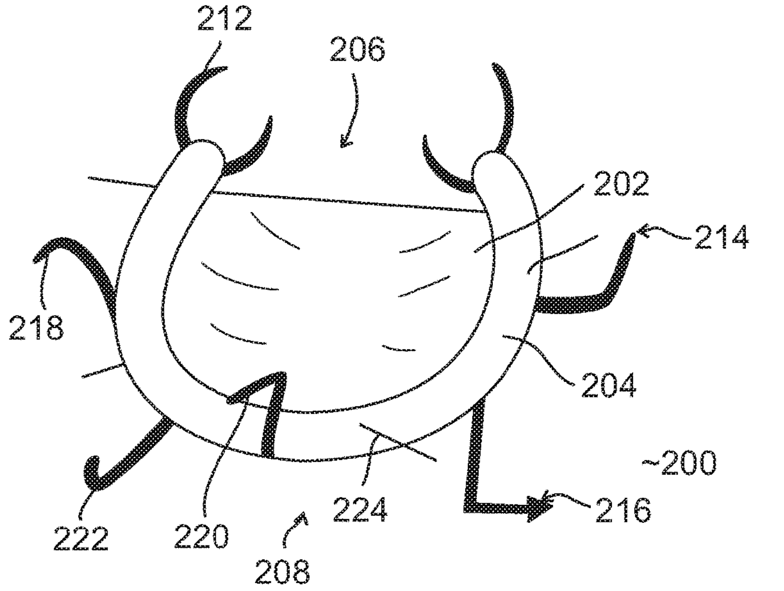
FIGS. 2A-2C are various views of an exemplary design of the tricuspid device, in accordance with an exemplary embodiment of the invention.
Figure 2B:
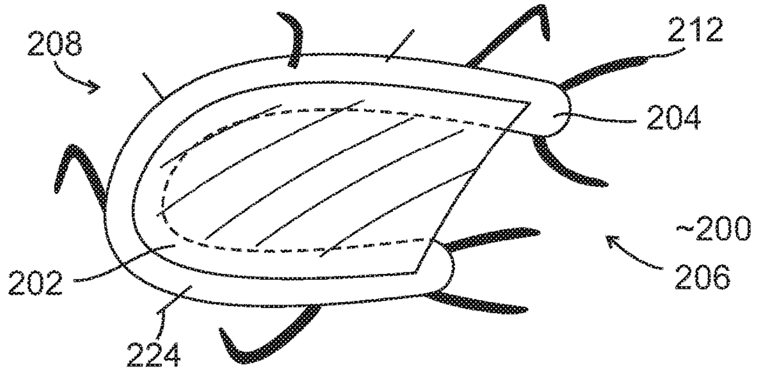
Figure 2C:
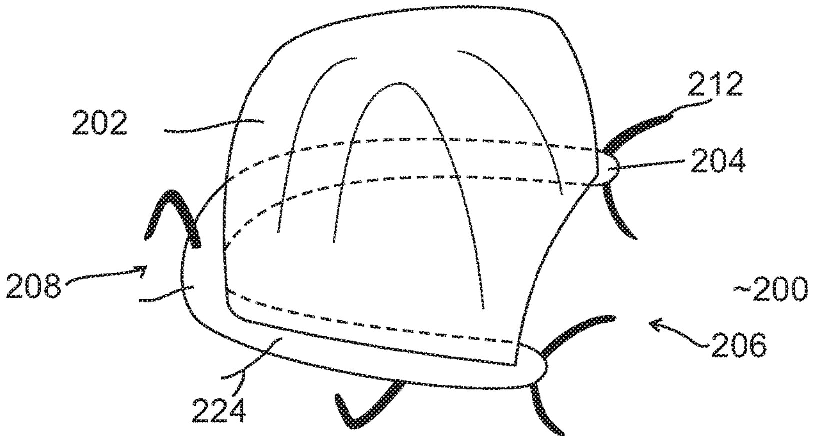

FIGS. 2A-2C illustrate various views of an exemplary design of prosthesis 200 to control blood flow through a right atrioventricular junction, such as prosthesis 120 of FIGS. 1B and 1C, in accordance with an exemplary embodiment of the invention.

In an exemplary embodiment of the invention, prosthesis 200 comprises at least one blood flow control element 202 to trap blood during systole. Optionally, prosthesis 200 is designed to encourage flow in its volume, such as in the case that no leakage is allowed. In a non-limiting example, prosthesis 200 includes a spring loaded part, so that blood flow control element 202 expands in two states. Alternatively, prosthesis can also merely block flow. FIG. 2A is a top view and FIG. 2B is an isometric view with blood flow control element 202 in a collapsed state. FIG. 2C is an isometric view with control element 202 in an expanded state.

In an exemplary embodiment of the invention, as shown in FIG. 2C, flow control element 202 is shaped to capture the volume of regurgitated blood. Non-limiting shapes include; cuboidal, cylindrical, cone, prism, pyramid ellipsoidal.

In an exemplary embodiment of the invention, blood flow control element 202 is a sail. Optionally, the sail is filled by blood flow to block the annulus. In some embodiments, sail leaks at least some blood flow. In some embodiments, the sail does not leak. Optionally, the sail collapses by back flow or by elasticity. Optionally, the collapsing sail releases the captured blood flow into the ventricle.

In some embodiments of the invention, blood flow control element 202 is a seal which does not capture blood. Optionally, the seal leaks. Alternatively, the seal does not leak.

In an exemplary embodiment of the invention, element 202 can be made out of one or more of a variety of biocompatible materials and/or coatings. Optionally, the material and/or coating is relatively resistant to calcification. Alternatively or additionally, the material is relatively durable. Alternatively or additionally, the material and/or coating prevents infiltration of cells such as epithelial cells. Alternatively, the material and/or coating allows and/or encourages growth of cells.

In an exemplary embodiment of the invention, element 202 is made out of biological materials, Non-limiting examples include porcine pericardium, bovine jugular vein valve leaflets, porcine small intestinal submucosa. Alternatively or additionally, element 202 is made out of synthetic biocompatible materials, non-limiting examples include polyurethane (e.g., Bionate), polystyrene-b-polyisobutylene-b-polystyrene (SIBS), polyetheretherketone (PEEK), polytetrafluoroethylene (PTFE), and/or Polynivyl alcohol cryogel (PVAC).

In some embodiments of the invention, a suitable blood flow control element (e.g., pericardium) is sewn directly onto the annulus as treatment.

In an exemplary embodiment of the invention, the thickness of element 202 is about 50 micrometers, or about 75, about 100, about 150, about 200, about 250, about 300, about 350, about 400 micrometers, or other smaller, intermediate or larger thicknesses are used. The thickness can be selected to meet trade offs, for example, the relatively thinner thickness potentially results in a smaller delivery profile (e.g., when compressed for percutaneous delivery) and/or in a relatively smaller pressure force required to urge (e.g., expand and/or open) element 202. For example, the relatively thicker thickness potentially results in a relatively more durable prosthesis 200. Optionally, the thickness can be non-uniform, varying across element 202, for example, being relatively thicker in areas that experience relatively more stress such as commissural points. Optionally, non-uniform thickness is used to control its collapsing during diastole.

In an exemplary embodiment of the invention, element 202 is elastic, being able to expand (e.g., under pressure conditions in the right ventricle of at least 5 mmHg, at least 10 mmHg, at least 15 mmHg, at least 20 mmHg, at least 30 mmHg, at least 40 mmHg, or other smaller, intermediate or larger values are used) at least 5%, at least 10%, at least 20%, at least 30%, at least 50%, at least 75%, at least 100%, or other larger or intermediate percentages. Alternatively or additionally, element 202 has elastic wires and/or threads. Alternatively, element 202 is relatively inelastic, being able to expand less than 5%.

In an exemplary embodiment of the invention, blood control element 202 is mechanically coupled to a support 204. Non-limiting examples of coupling include; gluing, stitching, crimping. Optionally, support 204 is at least partially coated by a continuation of element 202, for example, element 202 is continuous with the coating; preventing and/or reducing areas of discontinuity.

In an exemplary embodiment of the invention, support 204 is substantially rigid and/or resilient. In alternative embodiments, at least sections or all of support 204 is very flexible and/or soft so that it conforms to the geometry of the heart and/or changes thereof.

Exemplary Fixation of the Prosthesis

Referring to FIGS. 2A-2C, in an exemplary embodiment of the invention, support 204 anchors at least some parts of element 202, providing one or more areas of stability.

In an exemplary embodiment of the invention, support 204 comprises a septal aspect 206 and a non-septal aspect 208.

In an exemplary embodiment of the invention, septal aspect 206 is adapted to be placed facing and/or opposite the membranous septum of the heart, the septum comprising at least some electrically conduction channels such as the AV-node and/or bundle of His. Optionally, the device is non-symmetrical, for example, septal aspect 206 is smaller and/or 'cut off' to prevent contact with at least some portion of the septum.

In an exemplary embodiment of the invention, septal aspect 206 is a 'missing' part of support 204, forming a gap and/or non-continuous portion between two ends of support 204. Optionally, when in position in the tricuspid annulus, prosthesis 200 (e.g., closest part of support 204) is at least 5 mm away from the septum, or at least 7 mm, 10 mm, 15 mm, 20 mm, away, or other smaller, intermediate or larger distances are used.

In an exemplary embodiment of the invention, non-septal aspect 208 is adapted to be placed against the tricuspid annulus, such as against the native leaflets (e.g., pushing leaflets against the annular tissue), against the commissural areas (where the leaflets attach to the fibrous ring of the annulus), above the leaflets against the muscle, against the fibrous ring of the annulus (e.g., leaflets missing such as removed by surgery and/or congenital disease), and/or against an implanted device (e.g., prosthetic valve and/or annuloplasty ring placed during a previous surgery).

In an exemplary embodiment of the invention, non-septal aspect 208 can be thought of as an ovoidal, circular and/or ellipsoidal circumference that is 'missing' an arc segment from a complete support 204. Optionally, the diameter or the longest dimension of support (e.g., if support 204 had a complete circumference) is suitable for patients without annulus dilatation, about 20 mm, about 22 mm, about 24 mm, about 26 mm, about 28 mm, about 30 mm, or other smaller, intermediate or larger distances are used. Alternatively, the diameter of support 204 is suitable for patients with annular dilatation, about 32 mm, about 34 mm, about 36 mm, about 40 mm, about 50 mm, about 60 mm, about 70 mm, about 80 mm, or other smaller, intermediate or larger values are used.

In an exemplary embodiment of the invention, support 204 is substantially planar. Alternatively, support is not planar, such as designed to fit the shape of the annulus, for example saddle shaped. In some embodiments of the invention, support 204 is designed to 'naturally' fall into place when implanted.

In an exemplary embodiment of the invention, support 204 is a ring or a partial ring, or other non-limiting examples of structures including a band, a wire, a rod. The cross sectional thickness of support 204 is about 100 micrometers, about 200, about 300, about 400, about 500, about 700, about 1000 micrometers, or other smaller, intermediate or larger thicknesses are used. The height of support 204 (e.g., distance across annulus as measured when in position) is about 1 mm, about 2 mm, about 5 mm, about 10 mm, about 15 mm, about 20 mm, about 25 mm, about 30 mm, or other smaller, intermediate or larger values are used. Optionally, the height is related to the height of a support element coupled to support, for example as will be described with reference to FIGS. 8A-8B.

In an exemplary embodiment of the invention, support 204 is shaped to fit the annulus, for example, by self-expanding to the designated shape. Alternatively, support 204 is forced to conform to the shape of the annulus, for example, by expanding a balloon inside support 204 and pushing support 204 against the annulus. In some cases, the state of the annulus is evaluated for the ability to be balloon expandable. In some cases, balloon expansion inside the annulus is not allowed, for example, if the balloon will distort the annulus to an unacceptable shape, such excessive dilation of an inelastic annulus. Alternatively, the annulus is made to fit the shape of support 204, for example, by surgically stitching the annulus to support 204.

In an exemplary embodiment of the invention, support 204 is relatively elastic and/or flexible, for example, yielding and/or conforming to the expansion and/or contraction of heart muscles during the cardiac cycle. For example, support 204 is able to expand and/or contract about 1%, about 5%, about 10%, about 20%, or other smaller, intermediate or larger sizes are used. Alternatively, support 204 is relatively rigid against the expansion and contraction of the heart muscles.

Non-limiting examples of a material used for support 204 include one or more of; self expanding metal (e.g., Nitinol), rigid metal (e.g., steel), polyurethane.

In an exemplary embodiment of the invention, prosthesis 200 is relatively smooth, for example, element 202, support 204 and/or coupling between 202 and 204. A potential advantage is that the smoothness prevents and/or reduces damage to red blood cells (e.g., shearing, lysis), formation of thrombus, formation of embolus and/or formation of calcification.

In some embodiment of the invention, prosthesis 200 comprises one or more attachment elements 210 coupled to support 204. Elements 210 secure prosthesis 200 in position in the annulus, preventing and/or reducing migration of prosthesis 200, such as due to pressure gradients (e.g., from blood flow) and/or due to the beating of the heart. Optionally, elements 210 maintain the open state of prosthesis 200 against the annulus, preventing prosthesis 200 from returning to at least a partially compressed state, such as due to contraction of the heart and/or due to temperature differences (e.g., if using a self expanding material that is temperature dependent such as Nitinol). Alternatively, prosthesis 200 is elastically predisposed to expand outwards or contract inwards, and elements 210 such as staples hold it in place.

In some embodiments of the invention, attachment elements 210 have a sharp tip 214 at the free end. Tip 214 is adapted to pierce tissue, such as the annular tissue and/or leaflets. Optionally, elements 210 are shaped to prevent and/or reduce removal from tissue, such as having an arrow head 216 free end. A potential advantage is reduced risk of migration and/or dislodging of prosthesis 200 from position. Alternatively, elements 210 are shaped to be removable from tissue, such as having a smooth 218 free end. A potential advantage is the ability to reposition prosthesis 200, such as during deployment and/or after deployment. Alternatively, elements 210 have other shapes adapted for other methods of fixating to the tissues. Non-limiting examples include; a rough surface to increase a frictional force with the tissue, having an adhesive attached at the end to glue to the tissue, graspers to pinch the tissue.

In some embodiments of the invention, attachment elements 210 are made out of any suitable material, optionally the same material as support 204.

Some non-limiting examples of attachment elements 210 are described with reference to; US application US 2005/0137701 by Salahieh et al., US application US 2010/0030328 by Segiun et al.

In some embodiments of the invention, at least one of attachment elements 210 is a septum attachment element 212. There are 2, 4, 6, 8 septum elements 212, or other smaller, intermediate or larger numbers are used.

In some embodiments of the invention, septum elements 212 are coupled to free ends of support 204 at septal aspect 206. Optionally, at least one septum element 212 is positioned to pierce the atrial septum. Optionally or additionally, at least one septum element 212 is positioned to pierce the ventricular septum. Septum elements 212 pierce to a depth of no more than 1 mm, 2 mm, 3 mm, 5 mm, 7 mm, 10 mm, or other smaller, intermediate or larger depths. In some embodiments, piercing is performed without perforation. Alternatively, elements 212 are flat contacts.

In some embodiments of the invention, septum elements 212 are positioned and/or spaced apart to not pierce the AV-node and/or bundle of His. Septum elements 212 are about 5 mm apart, about 7 mm, about 9 mm, about 11 mm, about 13 mm, about 15 mm, about 20 mm, about 24 mm apart, or other smaller, intermediate or larger values are used.

In some embodiments of the invention, at least one of attachment elements 210 is attachable to the annulus of the tricuspid valve, such as to the tissues and/or to the leaflets. Optionally, at least one atrial attachment element 220 is adapted to attach to the atrial aspect of the annulus. For example, by having a hook shape, extending upwards from the attachment at support 204 and then downward at the free end. For example, piercing at an angle of about 15 degrees relative to the tissue, or about 30 degrees, 45 degrees, 60 degrees, 75 degrees, or other smaller, intermediate or larger values are used.

Optionally or additionally, at least one ventricular attachment element 222 configured to be attached to the ventricular aspect of the annulus. For example, by having a hook shape, extending downward from the attachment at support 204 and the upwards at the free end. Optionally or additionally, at least one annular attachment element 224 is configured to be attached to tissues at the annulus (e.g., leaflets, muscle, fibrous tissue). For example, by having a straight shape, and jutting out from about a center of support 204. FIG. 7C is a non-limiting example of a tricuspid prosthesis anchored via ventricular and/or atrial attachment elements.

In some embodiments of the invention, prosthesis 200 is adapted for other attachment methods. Optionally, prosthesis 200 is adapted for suturing. For example, annulus support 204 contains one or more holes. Alternatively or additionally, prosthesis 200 is adapted for gluing. For example, annulus support 204 contains a glue and one or more holes. The glue can be pushed out through holes to attach to the tricuspid annulus.

In some embodiments, spacing between support elements 210 (e.g., elements 220, 222 and/or 224) along the circumference of support 204 is about 1 mm, about 3 mm, about 5 mm, about 7 mm, about 10 mm, about 15 mm, about 20 mm, or other smaller, intermediate or larger values are used.

In some embodiments, the cross sectional diameter of elements 210 (e.g., elements 220, 222 and/or 224) is about 0.1 mm, about 0.3 mm, about 0.5 mm, about 0.7 mm, about 0.9 mm, about 1.0 mm, about 1.5 mm, about 2 mm, about 3 mm, or other smaller, intermediate or larger values are used. Optionally, the diameter is uniform, except for a tapered tip region. Alternatively, the diameter is non-uniform, element 210 being tapered to the tip.

Although device 200 is described herein as being delivered and deployed using percutaneous techniques, this is not meant to be limiting. Some embodiments of device 200 can be implanted using other methods such as open heart surgery or through the apex of the heart (e.g., endoscopy).

Although device 200 has been described as being placed in the tricuspid annulus, and for this use may be especially advantageous as well as possibly solving previously unsolved problems, this is not meant to be limiting. Some embodiments of device 200 can be positioned and/or configured for use in place of and/or in addition to other valves of the heart (e.g., aortic, pulmonary, mitral) and/or in place of other valves in the body (e.g., venous). Some embodiments of device 200 can be used to create valves where none normally exist, such as in the inferior and/or superior vena cava. Some non-limiting examples of adapting device 200 for other positions in the body:

Mitral valve replacement—In most cases, the pressures within the left ventricle and/or atrium are significantly higher than on the right side. The device can be adapted to function under the higher pressures, for example, by making the blood flow control element relatively more rigid. In another example, the annulus of the device is designed to fit the anatomy of the mitral valve annulus.

Venous valve—In most cases, pressures within the venous system are significantly lower than those in the heart. The device can be adapted to function under the lower pressures, for example, the blood flow control element is relatively more flexible.

Exemplary Tricuspid Prosthesis Function

Figure 1D:
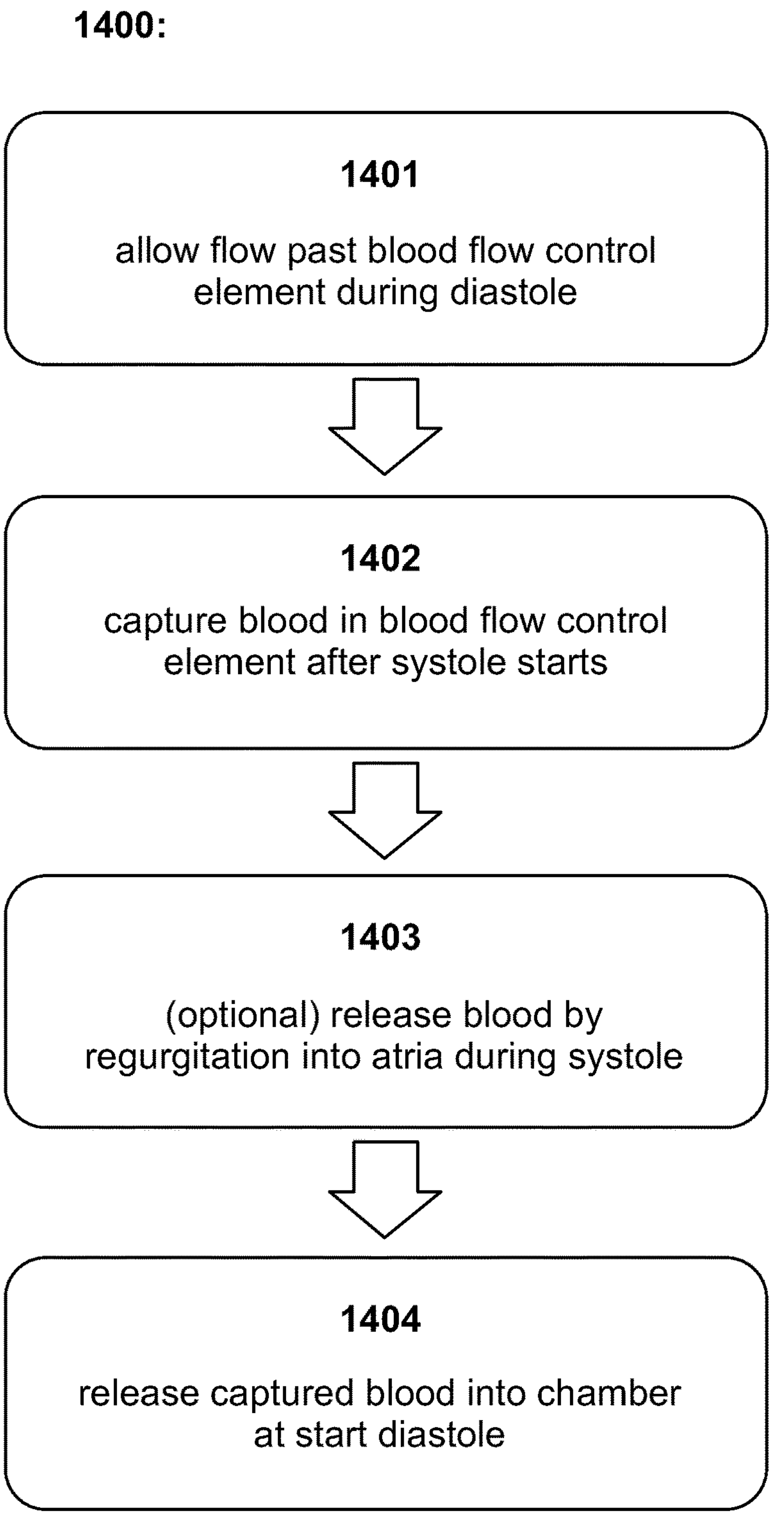
FIG. 1D is a flowchart of a method of operation of the tricuspid device, in accordance with an exemplary embodiment of the invention.

FIG. 1B illustrates the function of an implanted tricuspid prosthesis 120 in heart 100 during systole, such as prosthesis 200 described with reference to FIGS. 2A-2C, in accordance with an exemplary embodiment of the invention. Reference will also be made to FIG. 1D, which is a method 1400 of operation of the tricuspid prosthesis, such as prosthesis 200, in accordance with an exemplary embodiment of the invention. Ventricle 106 is contracting and/or in the contracted state, as shown by the small arrows. Atrium 104 is in the relaxed state.

In an exemplary embodiment of the invention, prosthesis 120 is deployed percutaneously. Other non-limiting methods of deployment include; transapical minimally invasive surgery, open heart surgery, open chest surgery. In open surgery, thread based suturing and/or clips are optionally used for attachment.

At 1401, for example during diastole, blood flow control element of prosthesis 120 does not substantially, or does to a lesser extent, impede blood flow from the atria to the ventricle.

At 1402, in systole, blood flow control element of prosthesis 120, such as the sail, captures at least some of the blood flowing from right ventricle 106 to right atrium 104, in accordance with some embodiments of the invention. Optionally, the element expands to capture at least some portion of the regurgitated blood volume therein.

In an exemplary embodiment of the invention, prosthesis 120 reduces the volume of regurgitated volume of blood flow from ventricle 106 to atrium 104.

In an exemplary embodiment of the invention, prosthesis 120 captures at least some of blood 122 in right atrium 104. Optionally or alternatively, at least some of blood 122 is trapped by prosthesis 120 in right ventricle 106.

In some embodiments of the invention, the element blocks at least some portion of the regurgitated blood volume for example, by preventing some of the blood from leaving ventricle 106 into atrium 104.

At 1403, at least some blood is optionally allowed to leak into the atria. Optionally, this blood is released from the blood control element (e.g., via one or more apertures therein). Optionally or alternatively, this blood is allowed to flow through the tricuspid valve, for example, due to no-coaptation of the leaflets of the valve with each other and/or prosthesis 120.

In an exemplary embodiment of the invention, prosthesis 120 provides pressure relief to right ventricle 106, thereby potentially allowing ventricle 106 to pump without being overloaded. Pressure relief is provided by allowing a volume of blood 124 to flow from ventricle 106 to atrium 104. Prosthesis 120 reduces the regurgitation, but still provides for at least some amount of blood 124 to regurgitate. A potential advantage of maintaining at least some regurgitation of blood through the tricuspid annulus is reducing the effects of the increase in blood volume on the right and/or left ventricles. The right ventricle may not be strong enough to adjust to the sudden increase in blood volume. Alternatively or additional, the left ventricle may not be strong enough to adjust to the sudden increase in blood volume coming from the right ventricle. Alternatively or additionally, the blood coming from the right ventricle might not be able to enter the left ventricle quickly enough (e.g., from the left atrium), such as due to a weak left atrium. It may be advantageous to find a balance in allowing some blood to leave the right ventricle. The workload on the left and/or right ventricle is thereby potentially reduced. Conditions such as pulmonary edema are potentially prevented and/or reduced.

In an exemplary embodiment of the invention, the volume of blood flow 128 out of ventricle 106 through a pulmonary valve 126 and into pulmonary artery 112 is relatively increased by prosthesis 120. Alternatively, blood flow 128 remains substantially the same. In an exemplary embodiment of the invention, the device is selected to have the desired effect of forward blood flow 128.

In an exemplary embodiment of the invention, deployed prosthesis 120 and/or the method of implanting prosthesis 120 does not interfere with signal conduction through AV node 114 and/or bundle of His 116. Additional details are described below, for example with reference to FIGS. 7A-7C.

FIG. 1C illustrates heart 100 with implanted tricuspid prosthesis 120 during diastole, in accordance with an exemplary embodiment of the invention. Atrium 104 is shown as contracting or in the contracted state (shown by small arrows). Ventricle 106 is shown in the relaxed state.

At 1404, in diastole, blood flow control element of prosthesis 120 releases at least some blood flow captured therein (e.g., as in 1402) to ventricle 106, in accordance with some embodiments of the invention. Optionally, the element (e.g., sail) collapses due to elasticity and/or a reduction in pressure due to blood flow from right ventricle 106. Optionally or alternatively, the element collapses due to forward flow from atrium 104 to ventricle 106.

In an exemplary embodiment of the invention, prosthesis 120 allows a sufficient amount of blood flow 132 from atrium 104 to ventricle 106, such as over a relatively low pressure gradient between atrium 104 and ventricle 106. Optionally, prosthesis 120 does not significantly interfere with flow 132, for example, there is sufficient area for blood flow through the atrioventricular junction. Optionally, prosthesis 120 changes configuration (from that during systole) to assist, prevent or reduce disruption of flow 132, for example, blood caught in the blood flow element is released back into the ventricle.

In an exemplary embodiment of the invention, at least one of the native tricuspid leaflets is preserved. Optionally, septal leaflet 134 is preserved. Optionally, prosthesis 120 is designed to function with septal leaflet 134, for example, the blood flow control element substantially coapts with leaflet 134 during systole and/or an opening orifice is created between the blood flow control element and leaflet 134 during diastole.

In an exemplary embodiment of the invention, prosthesis 120 does not interfere with blood flow out of a coronary sinus 130. For example, prosthesis 120 does not block sinus 130 to a degree that affects the blood outflow and/or prosthesis 120 does not compress a part of a blood vessel portion of coronary sinus 130 to a degree that significantly affects the blood outflow. Details of a suitable support structure that allows blood flow out of the coronary sinus is described for example, with reference to FIGS. 8A-8B.

Alternative Embodiments of Blood Flow Control Element

Figure 3A:
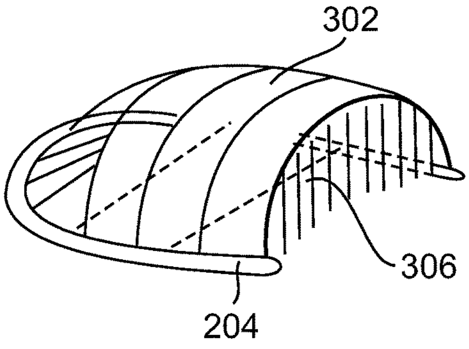
FIGS. 3A-3F are illustrations of some embodiments of a blood flow control element of the tricuspid device during diastole and systole, in accordance with an exemplary embodiment of the invention.
Figure 3B:
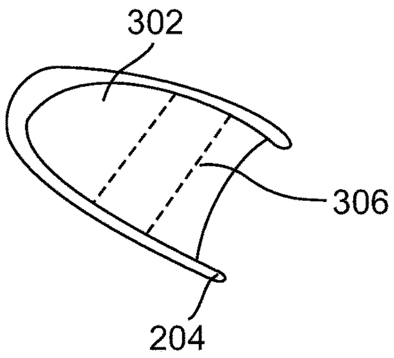
Figure 3C:
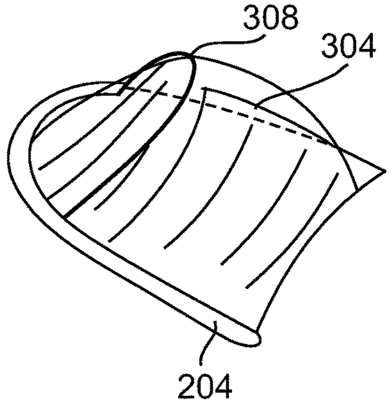
Figure 3D:
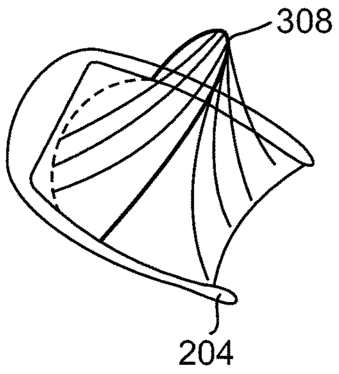
Figure 3E:
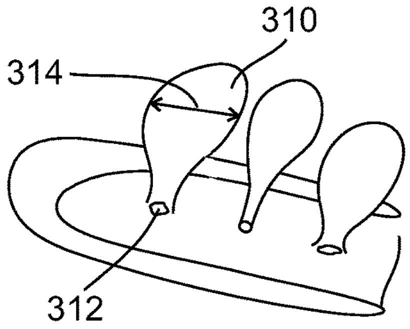
Figure 3F:
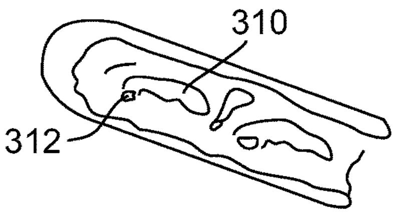

FIGS. 3A-3F illustrate some additional embodiments of the blood flow control element, in accordance with some embodiments of the invention. FIGS. 3A, 3C and 3E show the blood flow control elements in the expanded state, such as during systole. FIGS. 3B, 3D and 3F are corresponding figures showing the blood control elements in the contracted state, such as during diastole. The figures support broad interpretation of the other aspects, for example, of having one or two real leaflets, such as with a 300 degree annulus.

In some embodiments of the invention, the prosthesis comprises one or more inversion prevention members. Alternatively, the blood flow control element is designed not to invert (e.g., without using the prevention members), such as by using a relatively inflexible material. The inversion prevention members prevent and/or reduce the risk of blood flow control element entering the right ventricle, for example, during diastole (e.g., when blood is flowing from the right atrium to the right ventricle). Optionally, the blood flow control element has a non-uniform thickness, for example, with a greater thickness near a base (e.g., annulus) of the element, which provide inversion resistance. Optionally or alternatively, the element includes one or more pleats for folding during collapsing (e.g., during diastole). Optionally, the rest of element 120 is rigid enough so that once folded it will not push through the annulus of the tricuspid valve.

FIGS. 3A-3B are illustrations of a box-like or rectangular-like blood flow control element 302. Optionally, inversion prevention members 306 form a substantially planar block to movement of element 302 from the atrial aspect to the ventricle aspect, across the surface of support 204. For example, by spanning at least some of the distance between two areas of the support 204, such as spokes along the wheel of a bike. Blood flow during diastole is unable to entirely force element 302 into the ventricle. Non-limiting examples of members 306 include wires, bars, rods, strings. Non-limiting examples of the arrangement of members 306 include; in parallel, in a grid, in a star (e.g., crossing the center).

In an exemplary embodiment of the invention, element 302 includes at least one elastic element which serves to retract it towards support 204. For example, such an element may be an elastic cord which is attached between the peak of element 308 and support 204 (FIG. 3D). Optionally or alternatively, element 302 is itself elastic in this sense. Optionally or alternatively, element 302 is selected to have an elasticity weak enough to be overcome by systolic flow and thus element 302 expands, but which is not overcome by diastolic flow, so that element 302 can contract during at least part of the diastolic flow.

FIGS. 3C-3D are illustrations of some embodiments comprising at least one sail 304 design of the blood flow control element, for example, two sails 304. Optionally, sails 304 are supported and inversion is prevented and/or reduced by at least one arch 308 on the atrial aspect (e.g., will be positioned in the right atrium). Arch 308 is attached to at least two areas on support 204. Blood flow during systole fills sails 304, and flow during diastole collapses sails 304, at least in part. Optionally, collapse is due to elasticity of the sail or an elastic element therein, which element is stretched by the systolic pressure. Optionally, a plurality of such arches are provided. Optionally, the above mentioned elastic element is configured to bring the arches towards each other and/or support 204.

FIGS. 3E-3F are illustrations of at least one balloon 310 embodiment of the blood flow control element, for example, three balloons 310. Optionally, balloons 310 are filled with blood from the ventricle during systole. During diastole, balloons 310 at least partially deflate from the blood. Optionally, balloons 310 have an opening 312 with a relatively smaller diameter than an internal diameter 314. During diastole, inversion is prevented and/or reduced due to the relatively small opening 312, which makes it difficult for balloon 310 to invert through opening 312.

A potential advantage of expansion and collapse of the blood flow control element is prevention and/or reduction of blood stagnation. The contraction of the element forces the trapped blood to exit. Blood that is kept at motion is at a reduced risk of forming thrombus and/or emboli. A potential advantage is reduction and/or elimination of the dose of prescribed anticoagulant, such as Warfarin. In some embodiments of the invention, the sail can elute such a material.

Flow Control Blood while Allowing Regurgitation

FIGS. 4A-4C illustrate some embodiments of allowing at least some blood to regurgitate, in accordance with an exemplary embodiment of the invention. The embodiments can be one of the other embodiments described herein. Regurgitated blood flows from the right ventricle to the right atrium during the systolic phase of the heart cycle (contraction of the ventricle).

FIG. 4A illustrates prosthesis 200 implanted in a tricuspid annulus 402. Leaflet such as a septal leaflet 404 has been spared and continues to function. Leaflet 404 is shown in the ‘closed’ position during systole, and prosthesis 200 is shown in the expanded position. Regurgitated blood 406 (e.g., during systole) flows in a gap 408 between prosthesis 200 and leaflet 404.

FIG. 4B illustrates another embodiment of prosthesis 200 implanted in annulus 402, with spared leaflet 404. Prosthesis 200 is sized and/or positioned such that leaflet 404 contacts prosthesis 200 during systole, substantially forming a seal to regurgitated blood. Regurgitated blood 410 flows through one or more apertures 412 in blood flow control element 202. A potential advantage of the embodiment is relatively improved control over the size of the total area provided for regurgitation. Apertures may also be provided in other embodiments described herein.

FIG. 4C illustrates another embodiment of prosthesis 200. Regurgitated blood 414 flows between blood flow control element 202 and annulus 402, for example, through holes 416 created by one or more non-uniform support sections 418 that do not contact annulus 402. A potential advantage of the embodiment is providing support to the material of the blood flow control element at the location of the holes, to prevent and/or reduce tears. In a non-limiting example, element 202 is sail 304, for example as shown in FIG. 3C. A potential advantage of the sail embodiment is a relatively large area for regurgitation.

Flow During Diastole

Figure 5A:
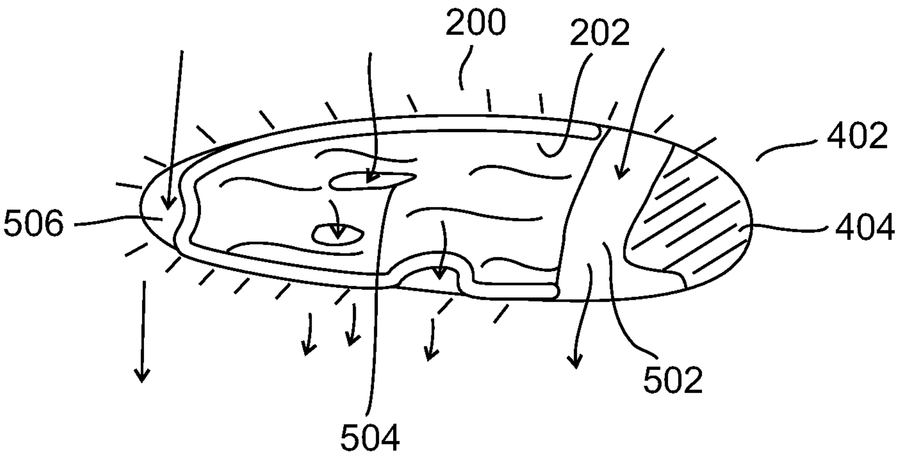
FIGS. 5A-5B are illustrations of blood flow with the tricuspid device in position during diastole, in accordance with an exemplary embodiment of the invention.
Figure 5B:
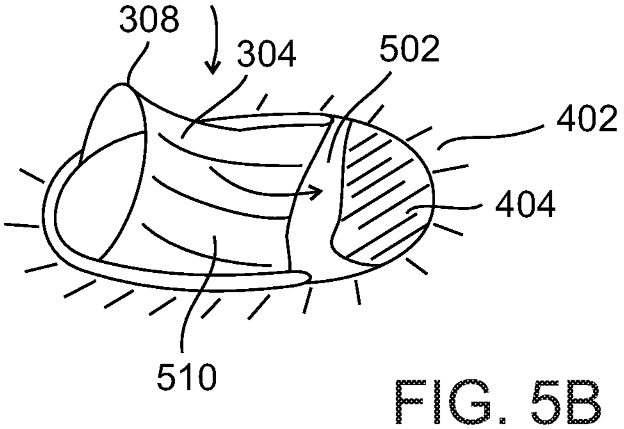

FIGS. 5A-5B illustrate some embodiments of the prosthesis, such as prosthesis 200, that allow for at least some flow of blood across the atrioventricular junction during diastole, in accordance with an exemplary embodiment of the invention. Flow of blood from the right atrium to the right ventricle during the diastolic state of the cardiac cycle provides blood to the right ventricle for pumping to the lungs during systole.

FIG. 5A illustrates prosthesis 200 positioned in annulus 402, during a compressed state (diastole), with optional preserved leaflet 404. Leaflet 404 is shown in the ‘open’ position. Diastolic filling can occur via one or more of; a gap 502 between blood flow control element 202 and leaflet 404, through one or more apertures 504 in element 202, and/or through one or more holes 506 between prosthesis 200 and annulus 402.

FIG. 5B illustrates a prosthesis having an inversion prevention element such as arch 308. Sail 304 is in the flattened state. Diastolic filling of blood is assisted by the sloping shape 510 of sail 304, for example, to direct blood to the ventricle such as through gap 502. A potential advantage is to relatively improve the flow of blood to fill the ventricle and/or prevent stagnation of blood.

In an exemplary embodiment of the invention, the flow during diastole is sufficient to fill the ventricle with blood. Accounting for the ejected volume, the flow is sufficient to fill the remaining unfilled portion of the ventricle. Optionally, the right ventricle is not overfilled, for example, flow is sufficient to allow the right ventricle to work effectively. For example, the amount of blood allowed is about 20 mL, about 30 mL, about 40 mL, about 50 mL, about 60 mL, about 70 mL, about 80 mL, about 90 mL, about 100 mL, or other smaller, intermediate or larger volumes are used.

In an exemplary embodiment of the invention, flow occurs during the ‘atrial kick’. The contraction of the atrium generates enough pressures to urge the prosthesis and/or leaflets to allow blood to flow into the ventricle. Alternatively or additionally, the flow occurs during the relaxation phase of the heart.

Optionally, the flow allowed is selected according to the patient. For example, patients with relatively dilated right ventricles are allowed more flow than patients with normal sized ventricles.

Alternative Design During Systole and Diastole

FIGS. 5C-5G illustrate a device 520 with asymmetric response to flow, in accordance with an exemplary embodiment of the invention.

Figure 5C:
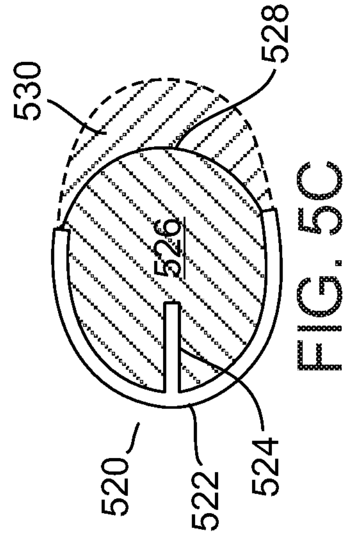
FIGS. 5C-5G illustrate a device with asymmetric response to flow, in accordance with an exemplary embodiment of the invention.

FIG. 5C is a top view of device 520 showing an elongate element 526 extending from an annulus/support 522 and coupled a sail/blood flow control element 526. Optionally, element 526 is coupled to sail 526 along its length. In an exemplary embodiment of the invention, element 524 does not extend to an edge 528 of sail 526, optionally extending (when viewed from a top projection) for a length of between 25% and 80% of element 526, for example, between 40% and 70%. Optionally, element 524 reaches to and/or defines the apex of sail 526. Also shown is an optionally spared natural leaflet 530. FIG. 5C shows device 520 during systole, with sail 526 filled.

Figure 5D:
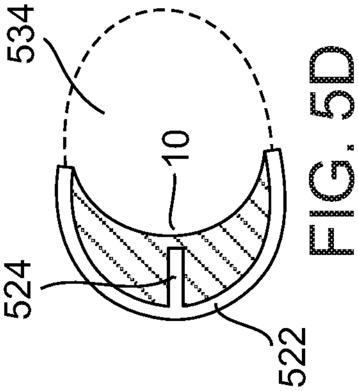
Figure 5E:
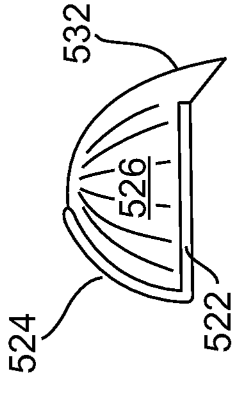

FIG. 5E is a side view of device 520 during systole. As can be seen, element 524 is optionally curved (but may be straight and/or may conform to the shape of sail 526 as the sail fills). In an exemplary embodiment of the invention, element 524 extends away from the plane of support 522 between 3 and 40 mm. Optionally or alternatively, the angle between the plane and element 524 is between 30 and 150 degrees, for example, between 30 and 70 degrees. It is noted that support 522 may not be flat, in which case the plane is defined as the flat plane having a smallest RMS distance to support 522.

Also shown in FIG. 5E is how sail 526 optionally extends past the edge of support 522, for example, defining a coaptation region 532 for contacting a different leaflet and/or for allowing some regurgitation therebetween.

In an exemplary embodiment of the invention, the curvature of sail 526 is selected to define a desired volume and/or level of coaptation. One or more suture in the sail may be used to reduce its volume, for example, for modification up or down of the captured volume and/or to control a degree of coaptation and/or regurgitation and/or conditions of coaptation. Optionally, such a suture may be attached or cut after implantation and/or may degrade on its own.

Figure 5F:
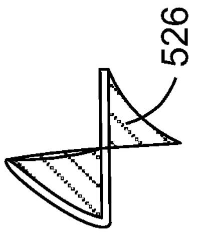

FIG. 5D and FIG. 5F show device 520 during diastole (top and side views), showing sail 526 collapsed (e.g., by flow from the atria) and including a substantially reduced capture volume. Optionally or alternatively, said 526 is elastic and collapses when systolic pressure and/or flow are not provided.

As can be seen, in some embodiments of the invention, blood flow is used to move a part of sail 526 in a direction perpendicular to the flow direction, so it is selectively interposed in the annulus of the tricuspid valve.

Figure 5G:
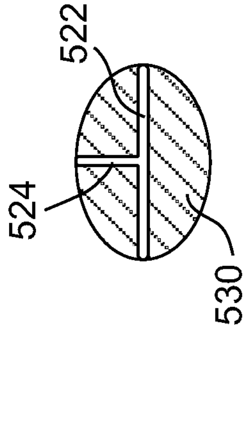

FIG. 5G is a front view along the plane of support 522. Reference 530 indicates a natural leaflet and/or coaptation area 532, depending on the implementation and size of area 532. In diastole, the area indicated by 530 would actually be portion 532 of sail 526.

In an exemplary embodiment of the invention, the connection between element 524 and support 522 is substantially rigid. In other embodiments, it is a hinge, for example, with a predefined degree of motion. Optionally or alternatively, support 522 acts as a torsion bar to resist rotation of element 524, with some motion allowed.

In an exemplary embodiment of the invention, element 524 is axially elastic and adapted to contract along its length, for example, by telescoping or by being defined as a plane of parallelograms which can change dimensions in the plane by changing their inner angles, for example, as used in some stent designs.

In an exemplary embodiment of the invention, element 526 is thicker and/or otherwise configured to resist bending towards the captured volume of sail 526 more than transverse bending.

Preservation of at Least One Leaflet

Figure 6A:
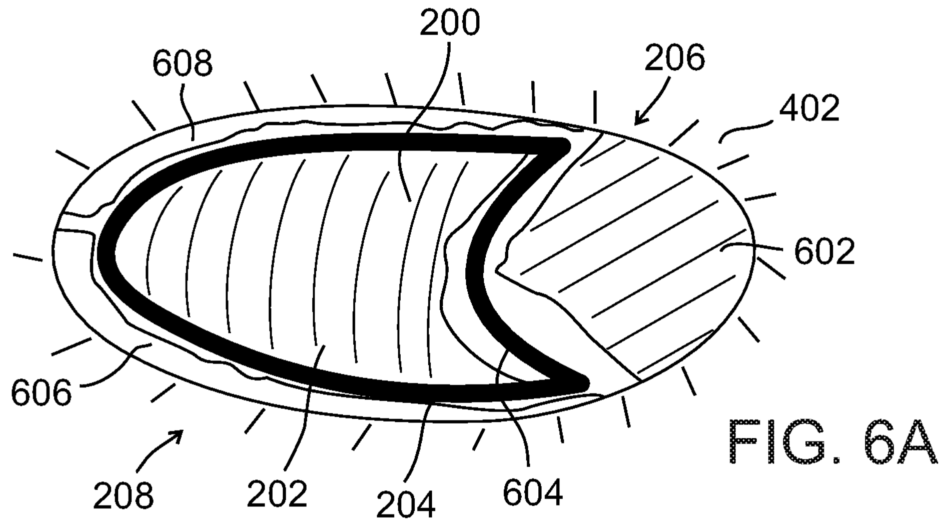
FIGS. 6A-6C are illustrations of the deployed tricuspid device sparing one or two native leaflets, in accordance with an exemplary embodiment of the invention.
Figure 6B:
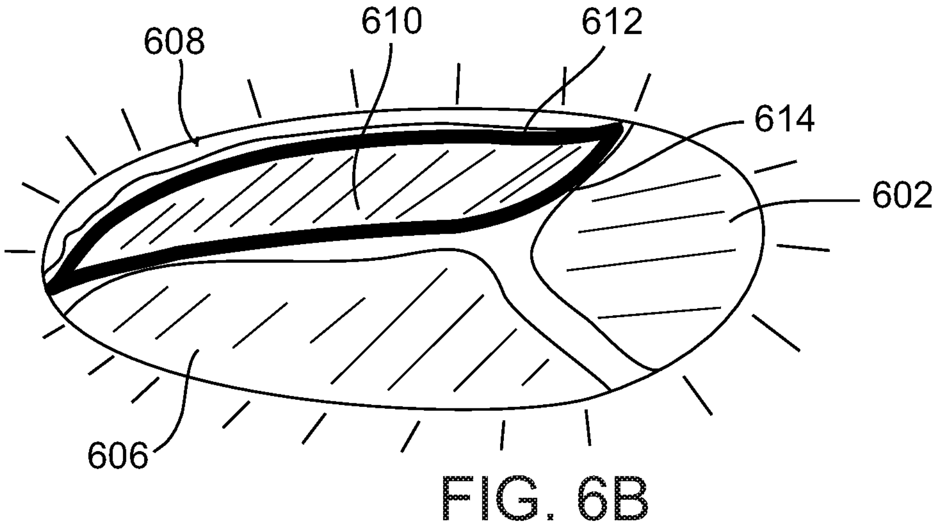
Figure 6C:
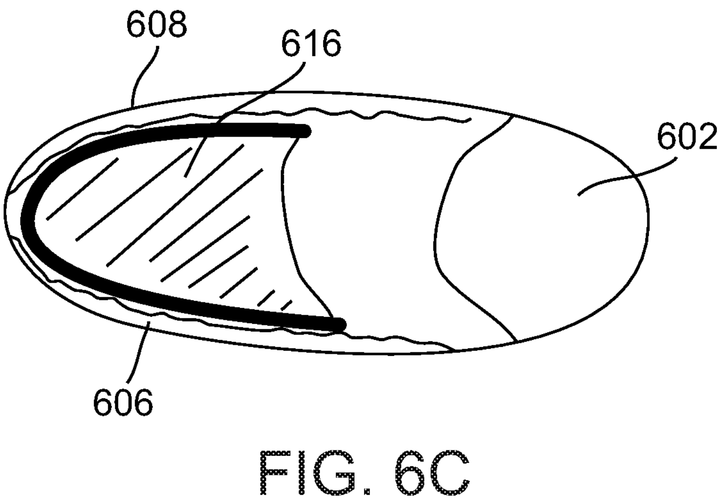

FIGS. 6A-6C illustrate embodiments of the prosthesis implanted in tricuspid annulus 402 while preserving the function of at least one native tricuspid leaflet, in accordance with an exemplary embodiment of the invention. Optionally, septal leaflet 602 is preserved.

FIG. 6A illustrates prosthesis 200 implanted in annulus 402. Support 204 is positioned against annulus 402, compressing and/or preventing function of anterior leaflet 606 and/or posterior leaflet 608. Support 204 and/or blood flow control element 202 are sufficiently away from any part of septal leaflet 602 so as not to interfere with the function of the preserved leaflet.

In some embodiments, support 204 includes a stability member 604. Alternatively, support 204 can be a non-expandable portion of the sail. Stability member 604 can extend between an anterior and posterior portions of support 204. Stability member 604 can be a continuation of support 204, such as being made out of the same material and/or having the same cross sectional shape. Optionally, member 604 has a shape substantially similar to an edge of leaflet 602 in the closed position, for example, an arc of a circle. Optionally, leaflet 602 coapts with member 604 during systole. Alternatively, the distance between support 204 and leaflet 602 is maintained by the shape of member 604.

FIG. 6B illustrates a prosthesis 610 that disables one leaflet and maintains the function of two leaflets. The function of septal leaflet 602 is maintained, along with one of anterior leaflet 606 or posterior leaflet 608.

In some embodiments of the invention, prosthesis 610 is sized, such as to disable one or two leaflets, or parts thereof. In a non-limiting example, the support of prosthesis 610 is axially extendible, so one size can fit several circumstances.

In some embodiments of the invention, the prosthesis has one or more radio-opaque markers. For example, positioned around the circumference of support 204. Alternatively or additionally, prosthesis has one or more ultrasound reflectors.

In some embodiments, support 612 of prosthesis 610 includes a relatively long stability member 614. For example, length of member 604 is about 100% of the length of support 612, or about 50%, about 70%, about 90%, about 100%, about 120%, about 140%, or other smaller, intermediate or larger values are used. FIG. 6A illustrates a partial length of member 614. FIG. 6B illustrates member 614 having a length longer than member 604. Optionally, member 614 has a shape similar to an edge of leaflet 602 and/or leaflet 606 in the closed position. Optionally, leaflet 602 coapts with leaflets 602/606 in systole. Alternatively, the distance between prosthesis 610 and leaflets 602 and/or 606 is maintained by the shape of member 614.

A potential advantage is to treat regurgitation in patients that have a tricuspid valve with relatively functioning leaflets, such as those with a dilated annulus.

FIG. 6C illustrates a prosthesis 616 that disables one or two leaflets and maintains the function of the remaining one or two leaflets, without overlaying the entire leaflet. Prosthesis 616 is anchored against no more than 30%, 50%, 70%, 90% of the edge of the leaflet (e.g., as measured along the annulus). A potential advantage is to create a relatively large distance between prosthesis 616 and septal leaflet 602, such as to allow a significant amount of blood to regurgitate.

Partial Circumference and/or Partial Anchoring

In an exemplary embodiment of the invention, the prosthetic device is designed to avoid contact and/or damage to nerves controlling contraction of the ventricles, such as AV-node 708 and/or bundle of His 710. Optionally, the prosthetic device is designed to avoid contact and/or damage with a margin of safety 720 around the nerves, for example, an area of the septum around the estimated area of the nerve tissue.

Figure 7A:
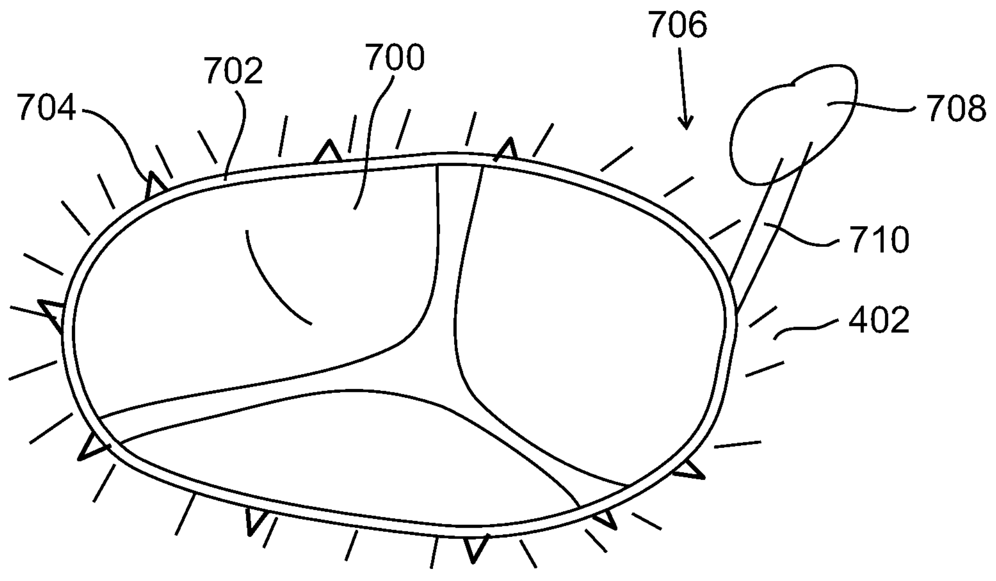
FIGS. 7A-7C are illustrations of the deployed tricuspid device preventing contact with the atrioventricular node and/or bundle of His, in accordance with an exemplary embodiment of the invention.
Figure 7B:
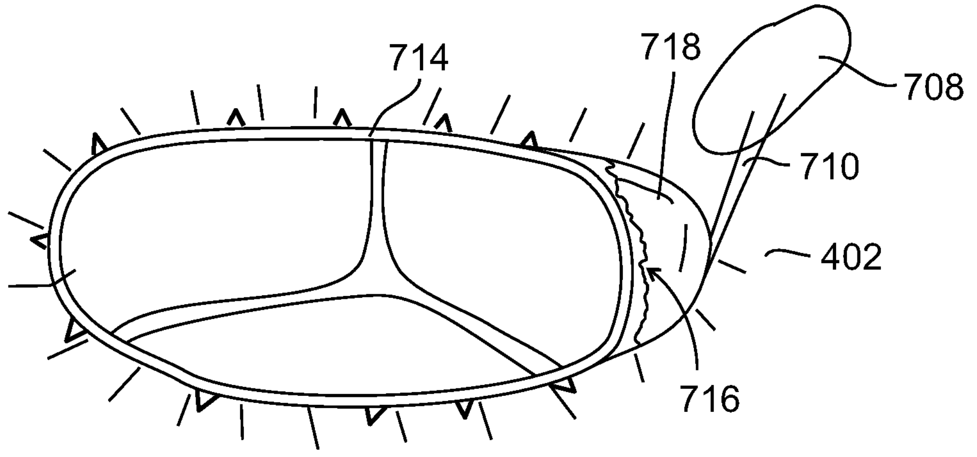
Figure 7C:
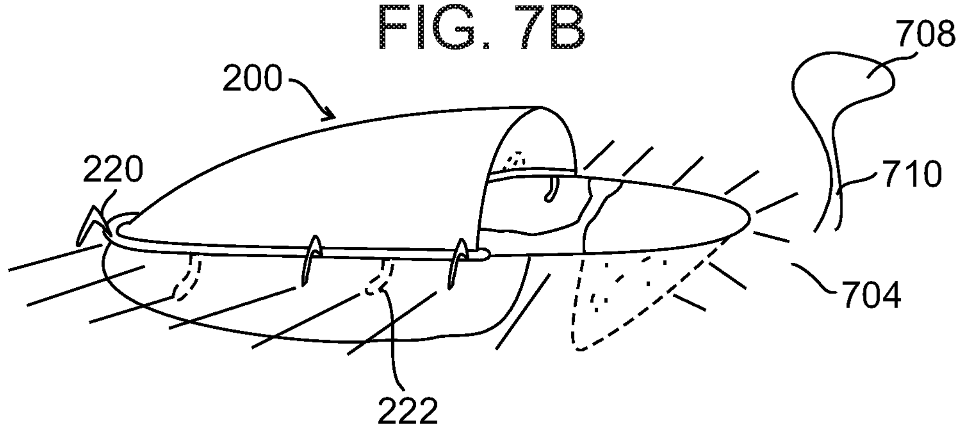

FIGS. 7A-7C illustrate embodiments of the prosthetic device in tricuspid annulus 402 having a partial circumference against annulus 402 and/or a partial circumference of anchors against annulus 402 (in a full or partial circumference), in accordance with an exemplary embodiment of the invention.

FIG. 7A illustrates prosthetic device 700 having a full circumference (e.g., of support 702) against annulus 402, but a partial anchoring against annulus 402 (e.g., using anchoring elements 704). In an exemplary embodiment of the invention, an anchor-free portion 706 is positioned against a section of septum containing AV-node 708 and/or bundle of His 710. The anchor free portion is about 15 mm long, or about 5 mm, about 10 mm, about 20 mm, about 25 mm, or other smaller, intermediate or larger lengths are used. The anchor free portion has an arc length of about 60 degrees, or about 30 degrees, about 45 degrees, about 90 degrees, about 120 degrees, or other smaller, intermediate or larger arc lengths are used.

FIG. 7B illustrates prosthetic valve 712 having a partial circumference of support 714. A portion 716 of support 714 does not contact the section of septum containing AV-node 708 and/or bundle of His 710. Optionally, septal leaflet 718 is rendered non-functional by the position of valve 712, for example, being partially compressed by portion 716, and/or movement of leaflet 718 is prevented or hindered by portion 716. The distance between portion 716 and the septal portion of node 708 and/or bundle 710 is about 1 mm, about 3 mm, about 5 mm, about 7 mm, about 10 mm, about 13 mm, about 15 mm, or other smaller, intermediate or larger distances are used.

Prosthesis devices 700 and/or 702 are not limited to a device to capture regurgitated blood, but can comprise of any device placed in the annulus of the tricuspid valve, such as tricuspid replacement valves of any design (e.g., single leaflet, bi-leaflet, tri-leaflet, mechanical and/or biological). A tri-leaflet biological valve is shown for illustration purposes and is meant to be non-limiting.

FIG. 7C illustrates prosthesis 200 of FIGS. 2A-2C in annulus 704, positioned away from AV node 708 and/or bundle of His 710. Optionally, prosthesis 200 is anchored by atrial attachment elements 220 and/or ventricle attachment elements 222.

In some embodiments of the invention, prosthesis 200 is anchored at a first anchoring location 724, either anteriorly or posteriorly. Optionally, prosthesis 200 is expanded in a direction away from the nervous tissue 722, for example, clockwise or anticlockwise, depending on first anchoring location 724. Additional details of deployment are provided, for example, with reference to FIG. 11.

In some embodiments of the invention, the design of the device to avoid damage and/or interference to the nerves is selected based on the ability to identify the location of the nerves and/or the ability to position the device away from the nerves. For example, in patients in which mapping of the nerves was not performed, the device having a relatively longer anchor-free portion and/or the device having a relatively shorter circumference are selected.

Delivery System—Support Structure

Figure 8A:
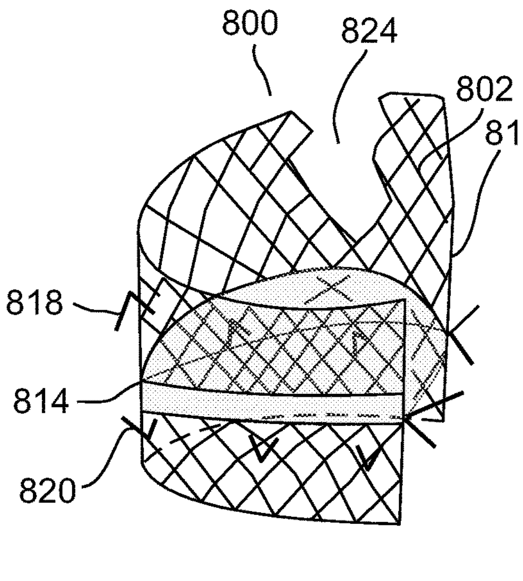
FIGS. 8A-8B are illustrations of some embodiments of support elements for percutaneous deployment of the tricuspid device, in accordance with an exemplary embodiment of the invention.
Figure 8B:
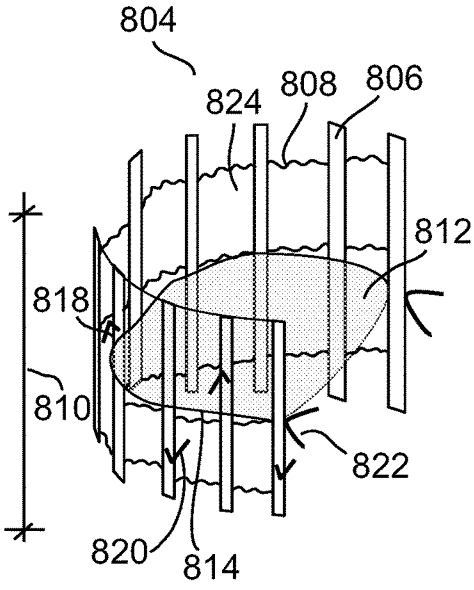

FIGS. 8A-8B are illustrations of some embodiments of radially expandable support elements for percutaneous delivery of the tricuspid prosthesis, in accordance with an exemplary embodiment of the invention. FIG. 8A is a support structure 800 made up of interlinked struts 802 in a cross ('X') formation, such as a Palmaz support element. FIG. 8B is a support element 804 made up of relatively straight beams 806 that are connected by members 808 that provide for expansion of space between beams 806, for example, the Edwards Sapiens valve.

In an exemplary embodiment of the invention, a blood flow control element 812 is coupled to support element 800 and/or 804. Optionally, element 814 is coupled to a support 814, support 814 being an integral part of and/or coupled to support element 800/804. Non-limiting examples of support 814 include a ring and/or a band of thicker and/or wider material. Alternatively, element 814 is coupled to support element 800 and/or 804 without support 814.

In a non-limiting example, US Applications Nos. 2006/0122686 and 2006/0122693 teach a method of coupling a device such as the blood flow control element to a support element such as support element 800 and/or 804. The applications also teach a support element design that can be radially expandable without damaging the coupled flow control element.

In an exemplary embodiment of the invention, support structure 800 is designed to not block the free leaflets (e.g., septal leaflet) by having a circumference substantially less than 360 degrees, for example, as described with reference to FIG. 6C.

In an exemplary embodiment of the invention, a length 810 of the support elements is longer than the thickness of the annulus. Alternatively, support element is shorter than the thickness, or about the same thickness. Support element length is about 10 mm, about 15 mm, about 20 mm, about 25 mm, about 30 mm, or other smaller, intermediate or larger values are used.

Figure 8C:
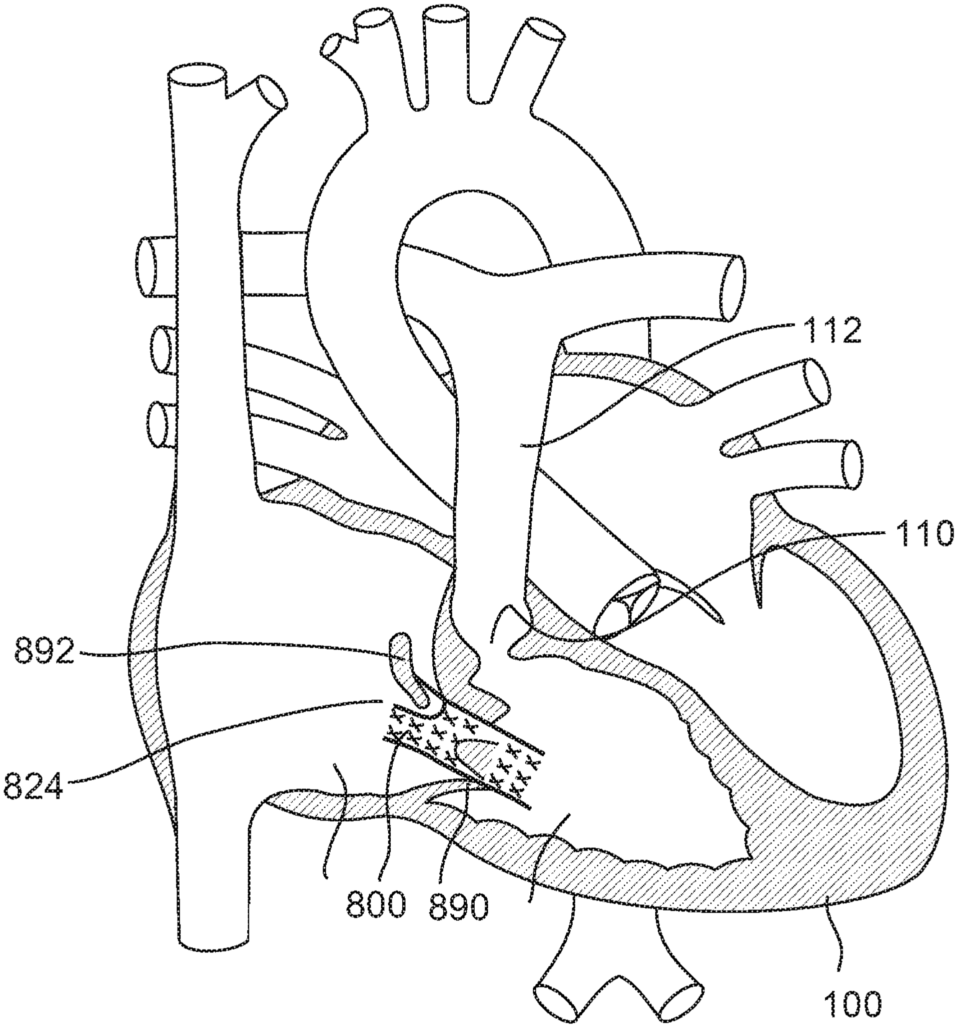
FIG. 8C is an illustration of a support element as in FIG. 8A, deployed in a tricuspid annulus, in accordance with some embodiments of the invention.

In an exemplary embodiment of the invention, support elements 800/804 have an aspect 824 to be placed facing the coronary sinus. The region of aspect 824 has a sufficiently large area to allow blood flow therethrough, so as not block blood flow out of the coronary sinus. Optionally, the area of aspect 824 is a hole in the support element wall, such as a relatively larger space between struts 802 and/or beams 806. Alternatively or additionally, the area of aspect 824 is a reduced height of the support element wall, at least in the coronary sinus aspect area. Hole of aspect 824 creates a contiguous area for blood flow within the wall of the support element of at least 1 $cm^2$, 2 $cm^2$, 3 $cm^2$, 4 $cm^2$, or other smaller, intermediate or large areas are used. FIG. 8C is a schematic illustration of a support element such as support element 800 deployed in a tricuspid annulus 890, in accordance with some embodiments of the invention. Support element 800 is deployed with aspect 824 positioned towards a coronary sinus 892 so as to allow at least some blood flow out of coronary sinus.

In an exemplary embodiment of the invention, the coupling of blood flow control element 812 to support element

800/804, optionally through support 814, is substantially within the middle of support element 800/804, or about 20%, 40%, 60%, 80%, 90%, from an atrial end 816 of support element 800/804, or other smaller, intermediate or larger values are used. Optionally, the position of element 812 within support element 800/804 is selected such that element 812 is entirely within the atrium when the tricuspid device has been deployed. Alternatively, the position of element 812 is selected such that at least a portion of element 812 is within the ventricle.

In an exemplary embodiment of the invention, support element 800/804 comprises anchoring elements, such as atrial anchors 818, ventricle anchors 820 and/or septal anchors 822. Optionally, atrial anchors 818 and ventricle anchors 820 are spaced apart along the circumference, for example, strut 806 has coupled thereto either anchor 818 or anchor 820 (e.g., alternating). A potential advantage will be described with reference to FIG. 9D below.

In an exemplary embodiment of the invention. The overall delivery profile of the support element and tricuspid device mounted thereon (e.g., retracted configuration for percutaneous implantation) is about 16 French, or 18 Fr, 20 Fr, 22 Fr, 24 Fr, 26 Fr, 28 Fr, 30 Fr, or other smaller, intermediate or larger values are used.

FIGS. 9A-9D illustrate some embodiments of the retracted state of support element 800/804 of FIGS. 8A-8B.

Figure 9A:
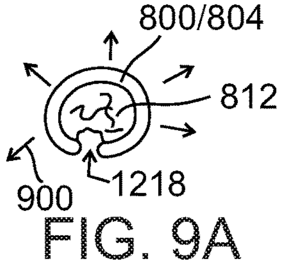
FIGS. 9A-9D are illustrations of various compacted states of the support element of FIGS. 8A-8B, in accordance with an exemplary embodiment of the invention.

FIG. 9A illustrates support element 800/804 having a smaller diameter in the retracted state than in the expanded state. Compression is in the radial direction, for example, spaces between struts 802 were substantially reduced, or spaces between beams 806 were substantially reduced. Expansion is in the opposite radial direction, as shown by arrows 900. Spaces are formed between struts 802 or beams 806.

Figure 9B:
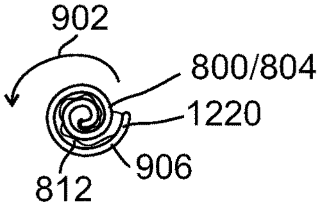

FIG. 9B illustrates support element 800/804 in a rolled retracted configuration. Expansion occurs by unrolling support element 800/804 in the direction of arrow 902.

Figure 9C:
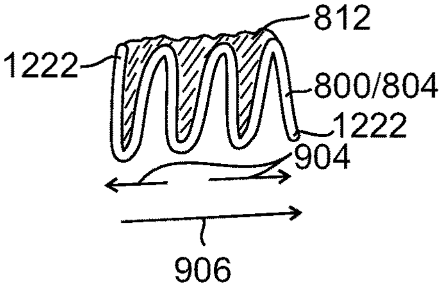

FIG. 9C illustrates support element 800/804 in a 'pleated' retracted configuration. Expansion occurs by 'stretching' out of support element 800/804, either in two directions as shown by arrows 904, or in one direction as shown by arrow 906. Optionally, the pleated configuration is rolled up as in FIG. 9B.

A potential advantage of the embodiments of FIGS. 9B-9C is reduced risk of contacting and/or perforating the sepal area containing the AV node and/or bundle of His, for example, using a method of deployment as described below with reference to FIG. 11. The advantage is potentially achieved by expanding the device in a direction away from the nerves.

Figure 9D:
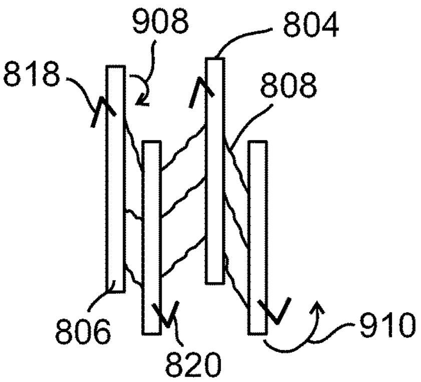

FIG. 9D illustrates support element 804 in an alternating biased configuration. Optionally, a portion of support element 804 having atrial attachment element 818 is biased relatively upwards. Alternatively or additionally, a portion of support element 804 having ventricle attachment element 820 is biased relatively downward. Upon deployment, support element 804 returns to the uniform configuration as shown in FIG. 8B, for example, portions having elements 818 move relatively down (shown by arrow 908) and/or portions having elements 820 more relatively up (shown by arrow 910). A potential advantage is the relatively improved anchoring in the atrium and/or ventricle, for example, using a method of deployment as described below with reference to FIG. 11.

Support element 804 as shown in FIG. 9D can be compressed as shown by the embodiments of FIGS. 9A-9C.

In an exemplary embodiment of the invention, the support element (e.g., support element 800/804) is self expanding. Non-limiting examples of self-expanding materials include; nitinol. Alternatively or additionally, support element 800/804 is balloon expandable. Non-limiting examples of balloon expandable materials include; stainless steel. Alternatively or additionally, support element 800/804 comprises at least some non-expandable materials. Non-limiting examples of non-expandable materials include hard plastics.

Figure 10A:
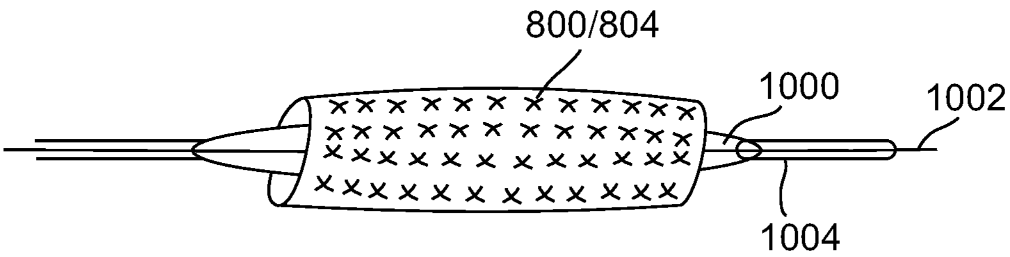
FIGS. 10A-10C are illustrations of a distal end of a catheter having the support elements of FIGS. 8A-8B assembled thereon ready for deployment, in accordance with an exemplary embodiment of the invention.
Figure 10B:
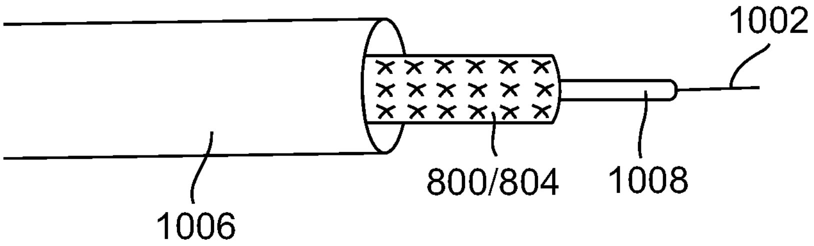
Figure 10C:
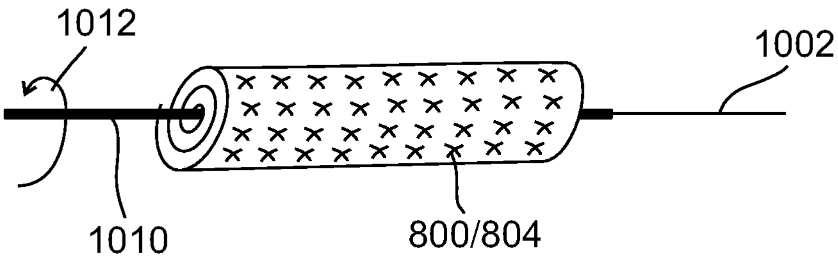

FIGS. 10A-10C illustrate embodiments of the support element mounted percutaneous tricuspid device in the retracted state on a distal end of a catheter, in accordance with an exemplary embodiment of the invention.

FIG. 10A illustrates the radially retracted support element configuration of the balloon expandable embodiment of support element 800/804 as in FIG. 9A, overlaying an expansion balloon 1000. Guidewire 1002 through distal end of catheter 1004 can be used to guide the prosthesis into position. Expansion of balloon 1000 forces the expansion of support element 800/804.

FIG. 10B illustrates the radially retracted support element configuration of the self-expanding embodiment of support element 800/804 as in FIG. 9A, covered by sheath 1006. Optionally, guidewire 1002 through distal end of catheter 1008 can be used to guide the prosthesis into position. Retraction of sheath 1006 allows support element 800/804 to self-expand.

FIG. 10C illustrates the rolled up configuration of support element 800/804, optionally in the pleated configuration, as shown in FIGS. 9B and/or 9C. Rod 1010 extending to outside of the body is used to unroll support element 800/804, such as by turning rod 1010 in the direction of arrow 1012.

In some embodiments of the invention, catheters are sold preassembled. The support element-mounted tricuspid prosthesis arrives on the distal end of the catheter. Alternatively, catheters and tricuspid prostheses are sold independently. The user assembles the prosthesis on the catheter, such as prior to implantation in the operating room. For example, by hand-crimping the device to the catheter.

Deployment of the Prosthesis in the Tricuspid Annulus

Figure 11:
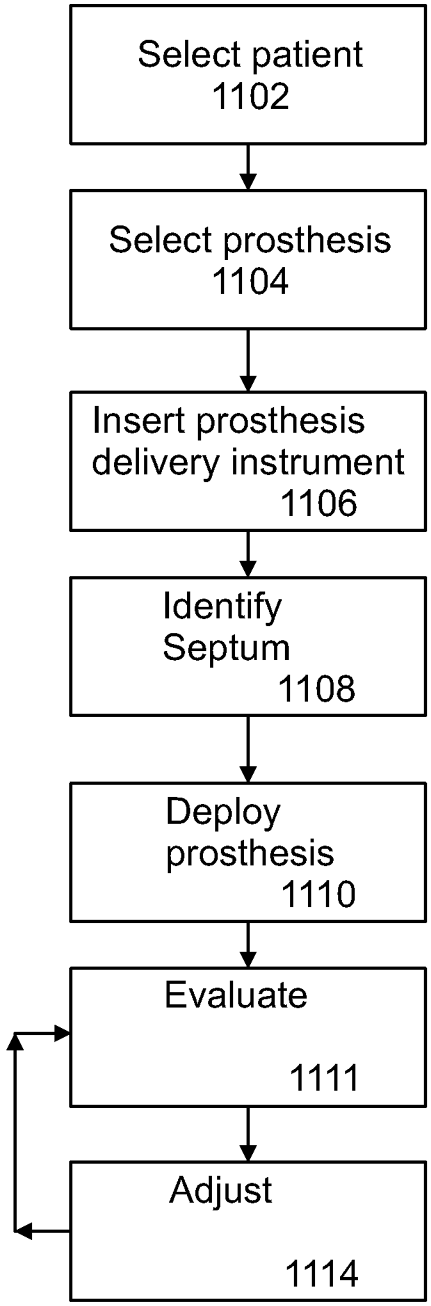
FIG. 11 is a flowchart of a method of deploying the tricuspid device, in accordance with an exemplary embodiment of the invention.
Figure 12:
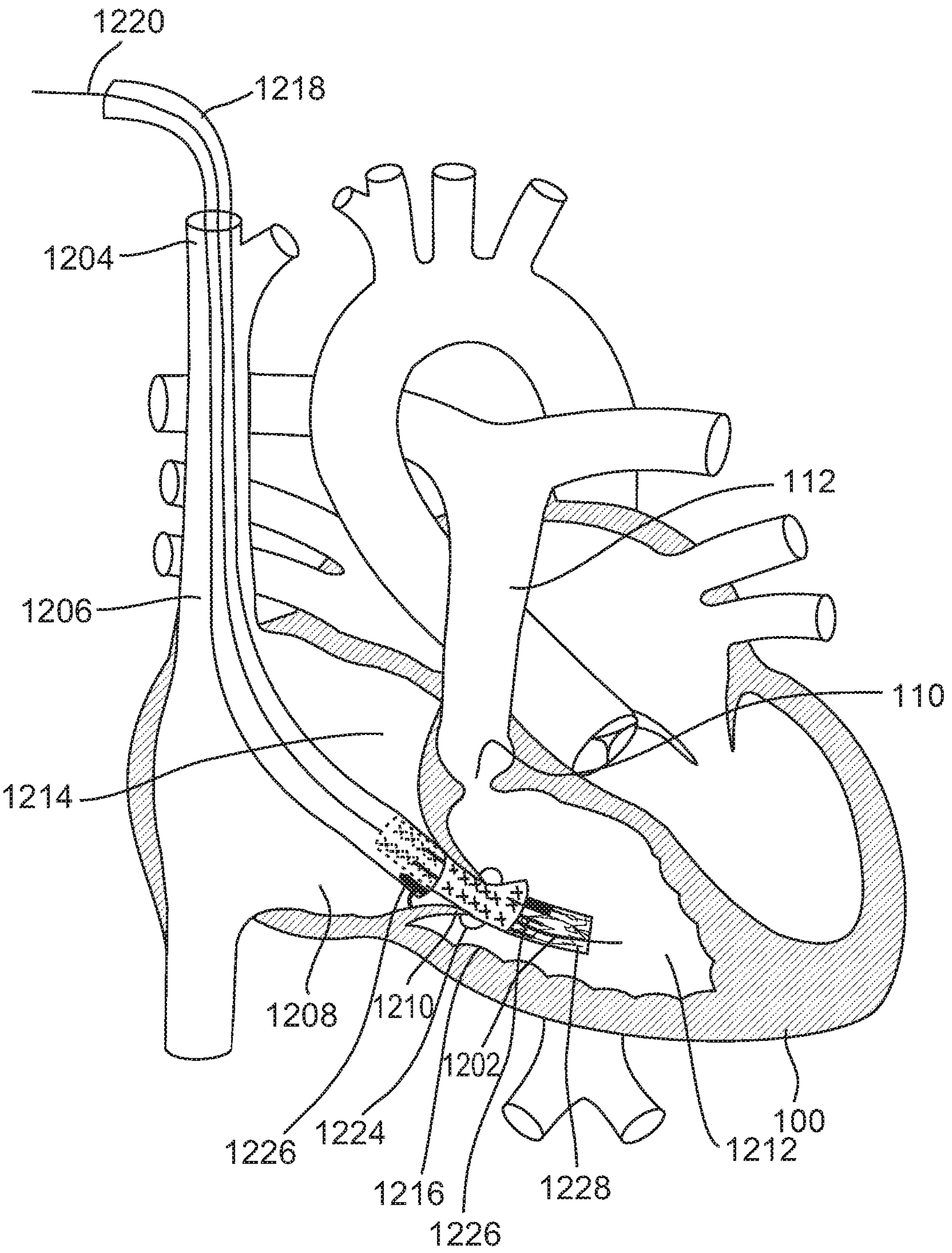
FIG. 12 is an illustration of the catheter of FIGS. 10A-10C deploying the support element mounted tricuspid device in the tricuspid annulus.

FIG. 11 is a method of deploying a tricuspid prosthesis in the tricuspid annulus, such as the device with expandable support structure as described with reference to FIGS. 8A and/or 8B, in accordance with an exemplary embodiment of the invention. Reference will be made to FIG. 12, which illustrates the percutaneous deployment of the prosthesis in the annulus, in accordance with an exemplary embodiment of the invention.

Optionally, at 1102 a patient is selected in accordance with some embodiments of the invention. In some embodiments, the patient has been diagnosed with tricuspid regurgitation, for example severe tricuspid regurgitation as defined by recommendations such as by Lancellotti et al.

Alternatively or additionally, the patient has been diagnosed with tricuspid stenosis. The stenosis is optionally treated by implantation of the device having a diameter larger than the current annulus, for example, the diameter being substantially the estimated diameter of the tricuspid annulus before the stenosis.

Alternatively or additionally, the patient has been diagnosed with a degenerated tricuspid prosthesis, such as a degenerated xenograft, or a degenerated device as described herein. The degeneration can be treated by implantation of the tricuspid device inside the current prosthesis, for example, as a ‘valve in valve’ implantation. A potential advantage is that the degenerated device does not have to be removed.

In some embodiments, the patient is elderly and/or a significant surgical risk (e.g., due to a past history of cardiac surgery and/or other comorbidities). The patient is stable enough to undergo treatment by percutaneous implantation of the valve.

Optionally, at 1104, the prosthesis for implantation in the patient is selected, in accordance with some embodiments of the invention. For example, different prosthesis are designed and sold to fit different patients. In some embodiments, the sail is selected to be attached directly to the old valve leaflets. Optionally, measurements of the patient’s anatomy and/or physiological condition are obtained, for example by ultrasound. Optionally, the parameters of the prosthesis are selected based on the measurements. For example, the volume of blood that the blood flow control element can capture is selected and/or adjusted based on the volume of regurgitated blood. For example, the diameter of the device is selected based on the measured diameter of the tricuspid annulus of the patient.

Optionally, at 1106, the type of implantation in the patient is selected. Optionally, the prosthesis will be delivered percutaneously, through the vasculature. Alternatively, the prosthesis will be deployed surgically, by open heart surgery. Alternatively, the prosthesis will be deployed in a minimally invasive manner, such as by endoscopic surgery through the apex of the heart.

In the embodiment in which the percutaneous route has been selected, the skin is punctured for access to the vascular system. Non-limiting examples include; the jugular vein (shown in FIG. 12), the subclavian vein, the femoral vein. Optionally, guidewire 1202 is threaded down through a jugular vein 1204, a superior vena cava 1206, a right atrium 1208, a tricuspid annulus 1210 and into a right ventricle 1212.

At 1108, an inter-atrial and/or inter-ventricular septum 1214 is located. Non-limiting examples include; by using imaging (e.g., fluoroscopy, ultrasound), by electrical methods (e.g., identifying electrical signals unique to the septum). In some embodiments, the location of the AV-node and/or bundle of His within the septum are identified.

At 1110, the prosthesis (e.g., prosthesis 1216) is deployed in the tricuspid annulus without piercing the membranous septum containing the AV-node and/or bundle of His. Catheter 1220 can be maneuvered proximally, distally, and/or oriented radially for the proper positioning.

In an exemplary embodiment of the invention, prosthesis 1216 is deployed by self-expansion, for example, by retracting sheath 1218. Optionally, the radially retracted configuration such as shown in FIG. 9A is used. Optionally, atrial aspect 1218 (e.g., non-continuous part of support element 800/804) is positioned facing septum 1214. Expansion can result in proper positioning of prosthesis 1216 within annulus 1210.

Alternatively, the rolled-up configuration as shown in FIG. 9B is used. Optionally, free end 1220 is positioned within annulus 1210, such as close to septum 1214, optionally without contacting septum 1214. The prosthesis is unrolled around annulus 1210, in a direction that does not overlap septum 1214 (e.g., anterior to posterior, or posterior to anterior), such as ‘away’ from septum 1214. In some embodiments of the invention, ‘unrolling’, optionally while anchoring, is accomplished by selectively releasing one or more anchors 1216 at a time. Optionally, a distal sheath 1228 positioned over the distal portion of device 1216 contains one or more slots 1226. Optionally, distal portion of proximal sheath 1218 contains slots 1226. Rotating sheath 1228 and/or sheath 1218 can release anchor 1216 through slot 1226. Retracting distal sheath 1228 and/or sheath 1218 can expand the respective distal and/or proximal ends of prosthesis 1216.

Alternatively or additionally, the pleated configuration as shown in FIG. 9C is used. One of the free ends 1222 is positioned within annulus 1210, such as close to septum 1214, optionally without contact. The prosthesis is unfolded around annulus 1210 in a direction that does not overlap septum 1214, for example, as described in the previous paragraph.

In some embodiments of the invention, the alternating biased configuration as shown in FIG. 9D is used. The alternating biased configuration can assist with anchoring of the prosthesis to annulus 1210. For example, retracted atrial attachment elements 818 and/or ventricle attachment elements 820 (shown in FIG. 12 as elements 1224) are positioned away from the respective anterior or posterior aspect during the alternating biased configuration. Upon return to the baseline configuration (e.g., by use of a memory metal such a Nitinol), elements 818 and/or 1224 fixate to the tissue. In some embodiments, rotation of distal sheath 1228 and/or sheath 1218 exposes elements 820 and/or elements 818. In some embodiments, retraction of distal sheath 1228 and/or sheath 1218 allows prosthesis to expand, and elements 820 and/or 818 can return to the unbiased position, thereby anchoring into annulus 1210.

Alternatively, prosthesis 1216 is deployed by balloon expansion, for example, by using the catheter embodiment of FIG. 10A.

In some embodiments, balloon expansion is performed prior to implantation of the prosthesis, such as to break calcification and/or fibrous tissue of the leaflets and/or annulus. In some embodiments, balloon expansion is performed after implantation of the prosthesis, such as to improve anchoring in the tissue.

In some embodiments, implantation of the tricuspid prosthesis is performed within an already implanted prosthesis. A potential advantage is replacement of a degraded prosthesis with a new prosthesis.

Optionally, at 1112 the patient is evaluated to determine the states of healing, in accordance with some embodiments of the invention. For example, the patient is evaluated to determine the extent of remodeling of the right ventricle as a result of implantation of the tricuspid device.

Optionally, the function of the implanted device is evaluated. For example, the device is evaluated to determine if the device is functioning as expected, such as by measuring the regurgitation through the device and/or effective orifice area. In another example, the device is evaluated to determine if the regurgitation is sufficient to allow for resistance caused, for example, by reduced left ventricle output and/or problems filling the left ventricle and/or right ventricle.

In some embodiments of the invention, the patient is evaluated immediately upon implantation. Optionally, the patient is evaluated upon follow up, optionally repeatedly, for example, after 1 day, after 2 days, after 1 week, after 2 weeks, after 1 month, after 2 months, after 3 months, after 6 months, or other smaller, intermediate or larger time periods are used.

Optionally, at 1114, adjustments are made to the device, in accordance with some embodiments of the invention. Optionally, adjustments are made in accordance with the evaluations as in 1112. Non-limiting examples include:

Replacement of a malfunctioning tricuspid device, such as by implantation of another device within the first device (e.g., 'valve in valve' deployment).

Relatively increasing the amount of regurgitation allowed by the device, such as in a patient with a right ventricle that is being overloaded by too much blood. In a non-limiting example, regurgitation is increased by making a slit in the blood flow control element.

Relatively reducing the amount of regurgitation allowed by the device, such as in a patient with a right ventricle that remodeled and/or adjusted to the increase in blood volume. In a non-limiting example, regurgitation is reduced for example by placing a stitch in the blood flow control element.

In an exemplary embodiment of the invention, a design such as described in one of U.S. Patent Publications:

US Application Publication No. 2012/0136436,

US Application Publication No. 2008/0262609, and/or

US Application Publication No. 2010/0286767, is used. For example, publication 2012/0136436 teaches an adjustable annulus for a mitral valve which is, in accordance with an exemplary embodiment of the invention, used to modify the annulus of a device as describe herein and/or a valve, so as to increase or decrease coaptation and thus affect regurgitation.

In an exemplary embodiment of the invention, the blood flow control element is tied using one or more degrading a suture, so that the element allows some regurgitation. Optionally, after a time, the suture dissolves or otherwise degrades and the flow control element increases in size, reducing regurgitation. Multiple such sutures or other elements may be provided and which may each degrade at a different time scale.

General

It is expected that during the life of a patent maturing from this application many relevant devices for placement in the tricuspid annulus will be developed and the scope of the term tricuspid device is intended to include all such new technologies a priori. As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A device for implantation at or near an annulus of a heart valve comprising:

at least one flexible blood flow control element having an expanded state with a convex shape sized to cover at least a portion of the annulus of the heart valve and said convex shape having an internal volume adapted to capture a volume of blood therein, and a curved support element configured to fit and be anchored to at least a portion of the annulus between an upstream chamber and a downstream chamber, said blood flow control element coupled to at least two points across said curved support element to extend said blood flow control element across said annulus when said curved support element is anchored to said annulus, said blood flow control element configured to extend away from said curved support element in said expanded state toward said upstream chamber such that said internal volume is at least partially inside an upstream chamber during downstream chamber systole when said curved support element is anchored to said natural annulus.

2. A device according to claim 1, wherein said internal volume is between 5 and 20 ml.

3. A device according to claim 1, wherein said support element is an at least partial ring adapted to contact and be anchored to at least a portion of said annulus including at least 120 degrees of a circumference thereof.

4. A device according to claim 1, wherein said support element is radially expandable.

5. A device according to claim 1, wherein said device comprises a plurality of tissue fixation elements, and at least some of said tissue fixation elements are positioned to fixate to at least one of a downstream aspect of said annulus and an atrial aspect of said annulus.

6. A device according to claim 1, wherein said support element has a non-symmetrical shape and said support element is adapted to have an open contiguous area of at least 1 cm2, said contiguous area is adapted to be placed towards a coronary sinus.

7. A device according to claim 1, wherein said support is sized to surround the natural annulus over an arc length of between 180 degrees and 360 degrees.

8. A device according to claim 1, wherein said support element is relatively rigid, said support element comprising a plurality of tissue fixation elements adapted to pierce tissue or otherwise interfere with conduction in-fixed to tissue; and a prosthetic valve or part thereof coupled to said support.

9. The device of claim 1, wherein said flow control element is coupled to only a portion of said support element such that blood is allowed to flow between said flow control element and said support element when said blood flow control element is in the collapsed state during downstream chamber diastole.

10. A device as in claim 9, wherein said flow control member includes a pleat for folding during said collapsed state.

11. A device as in claim 1, wherein said device is adapted for allowing at least some blood to regurgitate through said annulus during systole, wherein said at least some blood is between 3 and 25 mL and wherein said flow control element comprises one or more apertures for said regurgitation.

12. A device as in claim 1, further comprising an inversion prevention element extending from said support into a space between said flow control element and a downstream side of said support, said inversion prevention element blocking movement of said flow control element toward said downstream side of said support.

13. A device as in claim 1, wherein said flow control element is structured and selected to have an elasticity weak enough to be expanded by systolic flow, but which is not overcome by diastolic flow, so that said flow control element does not invert toward a downstream side of said support during diastolic flow.

14. A device as in claim 1, wherein said flow control member is of non-uniform thickness and wherein the thickness of the flow control element is increased in at least one location where the flow control member joins the base.

15. The device of claim 1, wherein said blood flow element is adapted to allow said volume of blood to flow backwards from the downstream chamber to the upstream chamber. through said annulus; the backward occuring during the time it takes for the blood flow element to reach said expanded state.

16. A device as in claim 1, wherein said upstream chamber includes at least one chamber selected from the group comprising a right atrium, a right ventricle, a left atrium and a left ventricle.

17. A device as in claim 1, wherein said downstream chamber includes at least one chamber selected from the group comprising a right ventricle, a pulmonary artery, a left ventricle, and an aorta.

18. A method of treating regurgitation in a heart valve of a patient in need of treatment thereof comprising:

percutaneously deploying a device into a heart valve annulus of the patient;

contacting a curved support element of the device to at least 45 degrees of the circumference of the heart valve annulus;

anchoring said support element to said heart valve annulus;

coupling a convex shapped blood flow control element to at least two points across the support element thereby extending the convex shaped blood flow control element across the heart valve annulus; and temporarily storing regurgitating blood from a downstream chamber of the patient in an upstream chamber of the patient in an inner volume of the convex shaped blood flow controlelement.

19. A method according to claim 18, said deploying including deploying in an annulus of a heart valve, said method further comprising expanding said device without said device contacting a membranous septum when in an implanted state.

20. A method as in claim 18, wherein said device is deployed without contacting at least one of an atrioventricular node and a bundle of His.

21. A method according to claim 18, comprising selecting said device to reduce an amount of regurgitated blood by 30%-80%, thereby treating said regurgitation.

22. A method according to claim 18, said device configured for:

capturing at least some volume of regurgitated blood in said blood flow control element during at least some part of systole; and releasing at least some volume of said captured blood into a downstream chamber during at least some part of diastole.

* * * * *

UNITED STATES PATENT AND TRADEMARK OFFICE

CERTIFICATE OF CORRECTION

PATENT NO. : 9,925,043 B2
APPLICATION NO. : 15/066051
DATED : March 27, 2018
INVENTOR(S) : Mordehay Vaturi It is certified that error appears in the above-identified patent and that said Letters Patent is hereby corrected as shown below:

On the Title Page

Item (73) Assignee: "Yokneam (JP)" should be changed to -- Yokneam (IL) --

Signed and Sealed this
Seventh Day of August, 2018

Andrei Iancu
*Director of the United States Patent and Trademark Office*